United States Patent
Haynes et al.

(10) Patent No.: US 7,101,552 B2
(45) Date of Patent: Sep. 5, 2006

(54) IMMUNOGEN COMPRISING AN HIV ENVELOPE PROTEIN, A LIGAND AND H2 PEPTIDE

(75) Inventors: Barton F. Haynes, Durham, NC (US); Dhavalkumar D. Patel, Durham, NC (US); Munir Alam, Chapel Hill, NC (US); Hua-Xin Liao, Chapel Hill, NC (US)

(73) Assignee: Duke University, Durham, NC (US)

( * ) Notice: Subject to any disclaimer, the term of this patent is extended or adjusted under 35 U.S.C. 154(b) by 78 days.

(21) Appl. No.: 09/960,717

(22) Filed: Sep. 24, 2001

(65) Prior Publication Data

US 2002/0086283 A1 Jul. 4, 2002

Related U.S. Application Data

(60) Provisional application No. 60/323,697, filed on Sep. 21, 2001, provisional application No. 60/323,702, filed on Sep. 21, 2001, provisional application No. 60/285,173, filed on Apr. 23, 2001, and provisional application No. 60/234,327, filed on Sep. 22, 2000.

(51) Int. Cl.
*A61K 39/395* (2006.01)

(52) U.S. Cl. ............... 424/178.1; 424/196.11; 424/208.1; 530/350; 530/826

(58) Field of Classification Search ......... 530/324–328, 530/826, 350; 424/196.11, 208.1, 178.1
See application file for complete search history.

(56) References Cited

U.S. PATENT DOCUMENTS

| | | | |
|---|---|---|---|
| 5,013,548 A | 5/1991 | Haynes et al. |
| 5,019,387 A | 5/1991 | Haynes et al. |
| 5,352,576 A | 10/1994 | Haynes et al. |
| 5,516,632 A | 5/1996 | Palker et al. |
| 5,518,723 A | 5/1996 | DeVico et al. |
| 5,843,454 A | 12/1998 | Devico et al. |
| 5,993,819 A | 11/1999 | Haynes et al. |
| 2001/0036461 A1 | 11/2001 | Haynes et al. |
| 2003/0147888 A1 | 8/2003 | Haynes et al. |
| 2004/0001851 A1 | 1/2004 | Haynes et al. |
| 2004/0039172 A1 | 2/2004 | Haynes et al. |
| 2004/0086506 A1 | 5/2004 | Haynes et al. |
| 2004/0132010 A1 | 7/2004 | Haynes et al. |
| 2004/0197344 A1 | 10/2004 | Haynes et al. |

FOREIGN PATENT DOCUMENTS

| | | |
|---|---|---|
| WO | WO 93/15750 | 8/1993 |
| WO | WO 95/29700 | 11/1995 |
| WO | WO 97/14436 | 4/1997 |
| WO | WO 01/56355 | 8/2001 |
| WO | WO 02/024149 | 3/2002 |
| WO | WO 03/039470 | 5/2003 |
| WO | WO 03/046137 | 6/2003 |
| WO | WO 2004009785 | 1/2004 |
| WO | WO 2004075850 | 9/2004 |
| WO | WO 2005016952 | 2/2005 |
| WO | WO 2005/028625 | 3/2005 |

OTHER PUBLICATIONS

Stamatatos et al, "Generation and Structural Analysis of Soluble Oligomeric gp140 Envelope Proteins Derived from Neutralization–Resistant and Neutralization–Susceptible Primary HIV Type 1 Isolates", AIDS Research and Human Retroviruses 16(10):981–994 (2000).

(Continued)

*Primary Examiner*—Jeffrey Stucker
(74) *Attorney, Agent, or Firm*—Nixon & Vanderhye P.C.

(57) ABSTRACT

The present invention relates, in general, to an immunogen and, in particular, to an immunogen for inducing antibodies that neutralize a wide spectrum of HIV primary isolates. The invention also relates to a method of inducing anti-HIV antibodies using same.

13 Claims, 31 Drawing Sheets

OTHER PUBLICATIONS

Figure 1:
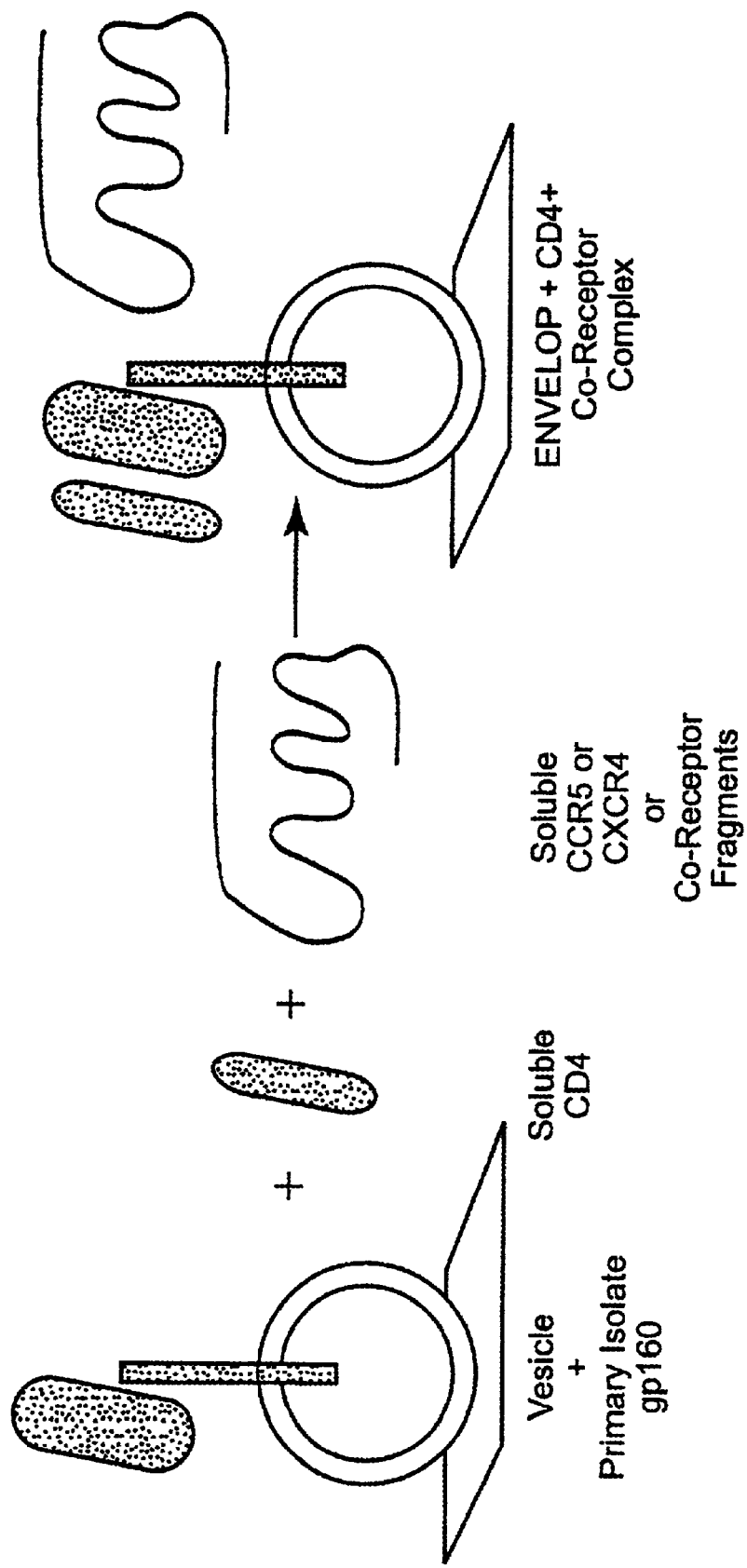

Hoffman et al, "Stable exposure of the coreceptor–binding site in a CD4–independent HIV–1 envelope protein", Proc. Natl. Acad. Sci. USA 96:6359–6364 (1999).

Golding et al, "Phorbol Ester–Induced Down Modulation of Tailless CD4 Receptors Requires Prior Binding of gp120 and Suggests a Role for Accessory Molecules", Journal of Virology 69(10):6140–6148 (1995).

Kwong et al, "Structure of an HIV gp120 envelope glycoprotein in complex with the CD4 receptor and a neutralizing human antibody", Nature 393:648–659 (1998).

Wyatt et al, "Involvement of the V1/V2 Variable Loop Structure in the Exposure of Human Immunodeficiency Virus Type 1 gp120 Epitopes Induced by Receptor Binding", Journal of Virology 69(9):5723–5733 (1995).

Trkoloa et al., "Human Monoclonal Antibody 2G12 Defines a Distinctive Neutralization Epitope on the gp 120 Glycoprotein of Human Immunodeficiency Virus Type1", Journal of Virology 70(2):1100–1108 (1996).

Mo et al, "Human Immunodeficiency Virus Type 1 Mutants That Escape Neutralization by Human Monoclonal Antibody IgG1b12", Journal of Virology 71(9):6869–6874 (1997).

Ye et al., "Association of Structural Changes in the V2 and V3 Loops of the gp 120 Envelope Glycoprotein with Acquisition of Neutralization Resistance in a Simian–Human Immunodeficiency Virus Passaged in Vivo", Journal of Virology 74(24):1955–11962 (2000).

Fouts et al, "Neutralization of the Human Immunodeficiency Virus Type 1 Primary Isolate JR–FL by Human Monoclonal Antibodies Correlates with Antibody Binding to the Oligomeric Form of the Envelope Glycoprotein Complex,", Journal of Virology 71(4):2779–2785 (1997).

Sullivan et al, "CD4–Induced Conformational Changes in the Human Immunodeficiency Virus Type 1 gp120 Glycoprotein: Consequences for Virus Entry and Neutralization", Journal of Virology 72(6):4694–4703 (1998).

Moore et al, "Exploration of antigenic variation in gp120 from clades A through F of human immunodeficiency virus type 1 by using monoclonal antibodies", Journal of Virology 68(12):8350–8364 (1994) –Abstract.

Jiang et al, "A Conformation–Specific Monoclonal Antibody Reacting with Fusion–Active gp41 from the Human Immunodeficiency Virus Type 1 Envelope Glycoprotein", Journal of Virology 72(12);10213–10217 (1998).

Rimsky et al, "Determinants of Human Immunodeficiency Virus Type 1 Resistance to gp41–Derived Inhibitory Peptides", Journal of Virology 72(2):986–993 (1998).

Earl et al, "Immunogenicity and Protective Efficacy of Oligomeric Human Immunodeficiency Virus Type 1 gp140", Journal of Virology 75(2):645–653 (2001).

Collman et al, "An infectious molecular clone of an unusual macrophage–trophic and highly cytopathic strain of human immunodeficiency virus type 1", Journal of Virology 66(12):7517–7521 (1992) –Abstract.

Munster et al, "A conserved neutralizing epitope on gp41 of human immunodeficiency virus type 1", Journal of Virology 67(11):6642–6647 (1993) –Abstract.

Cormier et al, "Specific interaction of CCR5 amino–terminal domain peptides containing sulfotyrosines with HIV–1 envelope glycoprotein gp120", PNAS 97(11):5762–5767 (2000).

Hoffman et al, "A Biosensor assay for studying ligand–membrane receptor interactions: Binding of antibodies and HIV–1 Env to chemokine receptors", PNAS 97(21):11215–11220 (2000).

Myszka et al, "Energetics of the HIV gp120–CD4 binding reaction", PNS 97(16):9026–9031 (2000).

Roben et al, "Recognition properties of a panel of human recombinant Fab fragments to the CD4 binding site of gp120 that show differing abilities to neutralize human immunodeficiency virus type 1", Journal of Virology 68(8):4821–4828 (1994) –Abstract.

Munster et al, "Cross–neutralizing activity against divergent human immunodeficiency virus type 1 isolates induced by the gp41 sequence ELDKWAS", Journal of Virology 68(6):4031–4034 (1994) –Abstract.

Earl et al, "Native oligomeric human immunodeficiency virust type 1 envelope glycoprotein elicits diverse monoclonal antibody reactivities", Journal of Virology 68(5):3015–3026 (1994) –Abstract.

Furata et al, "Capture of an early fusion–active conformation of HIV–1 gp41", Nature Struct. Biol. 5:276 (1998).

LaCasse et al, "Fusion–Competent Vaccines" Broad Neutralization of Primary Isolates of HIV , Science 283:357 (1997).

Boots et al, "Anti–Human Immunodeficiency Virus Type 1 Human Monoclonal Antibodies that Bind Discontinous Eptitopes in the Viral Glycoproteins Can Identify Mimotopes from Recombinant Phage Peptide Display Libraries", AIDS Research and Human Retroviruses 13(18):1549–1559 (1997).

Bieniasz et al, "HIV–1–induced cell fusion is mediated by multiple regions within both the viral envelope and the CCR–5 co–receptor", The EMBO Journal 16(10):2599–2609 (1997).

Wild et al, "Propensity for a leucine zipper–like domain of human immunodeficiency virus type 1 gp41 to form oligomers correlates with a role in virus–induced fusion rather than assembly of the glycoprotein complex", Proc. Natl. Acad. Sci. USA 91:12676–12680 (1994).

Collman et al, "An Infectious Molecular Clone of an Unusual Macrophage–Tropic and Highly Cytopathic Strain of Human Immunodeficiency Virus Type 1", Journal of Virology 66(12):7517–7521 (1992).

Alam et al, "T–cell–receptor affinity and thymocyte positive selection", Letters to Nature 381:616–620 (1996).

O'Shannessy et al, "Immunization Chemistries Suitable for Use in the BIAcore Surface Plasmon Resonance Detector", Analytical Biochemistry 205:132–136 (1992).

Mascola et al, "Immunization with Envelope Subunit Vaccine Products Elicits Neutralizing Antibodies against Laboratory–Adapted but Not Primary Isolates of Human Immunodeficiency Virus Type I", J, Infect. Dis. 173:340–348 (1996).

Rizzuto et al, "A Conserved HIV gp120 Glycoprotein Structure Involved in Chemokine Receptor Binding", Science 280:1949–1953 (1998).

Wyatt et al, "Involvement of the V1/V2 Variable Loop Structure in the Exposure of Human Immunodeficiency Virus Type 1 gp120 Epitopes Induced by Receptor Binding", Journal of Virology 69(9):5723–5733 (1995).

Robertson et al, Recombination in AIDs Viruses, J. Mol. Evol. 40:249–259 (1995).

Shu et al, Helical Interactions in the HIV–1 gp41 Core Reveal Structural Basis for the Inhibitory Activity of gp41 Peptides, Biochemistry 39:1634–1642 (2000).

Moore et al, "Exploration of antigentic variation in gp120 from clades A through F of human immunodeficiency virus type 1 by using monoclonal antibodies", Journal of Virology 68(12):8350–8364 (1994).

Collman et al, "An infectious molecular clone of an unusual macrophage–trophic and highly cytopathic strain of human immunodeficiency virus type 1", Journal of Virology 66(12):7517–7521 (1992).

Munster et al, "A conserved neutralizing epitiope on gp41 of human immunodeficiency virus type 1", Journal of Virology 67(11):6642–6647 (1993).

Roben et al, "Recongition properties of a panel of human recombinant Fab fragments to the CD4 binding site of gp120 that show differing abilities to neutralize human immunodeficiency virus type 1", Journal of Virology 68(8):4821–4828 (1994).

Munster et al, "Cross–neutralizing activity against divergent human immunodeficiency virus type 1 isolates induced by the gp41 sequence ELDKWAS", Journal of Virology 68(6):4031–4034 (1994).

Earl et al, "Native oligomeric human immunodeficiency virsut type 1 envelope glycoprotein elicits diverse monoclonal antibody reactivities", Journal of Virology 68(5):3015–3026 (1994).

Fouts et al, "Crosslinked HIV–1 envelope–CD4 receptor complexes elicit broadly cross–reactive neutralizing antibodies in rhesus macaques", PNAS 99(18):11842–11847 (2002).

Fouts et al, "Expression and Characterization of a Single–Chain Polypeptide Analogue of the Human Immunodeficiency Virus Type 1 gp120–CD4 Receptor Complex", Journal of Virology 74(24):11427–11436 (2000).

Devico et al, "Monoclonal Antibodies Raised against Covalently Crosslinked Complexes of Human Immunodeficiency Virus Tuype 1 gp120 and CD4 Receptor Identify a Novel Complex–Dependent Epitope on gp120", Virology 211:583–588 (1995).

Devico et al, "Covalently Crosslinked Coplexes of Human Immunodeficiency Virus Type 1 (HIV–1_gp120 and CD4 Receptor Elicit a Neutralizing Immune Response That Includes Antibodies Selective for Primary Virus Ioslates", Virology 218:258–263 (1996).

Vita et al, "Rational engineering of a miniprotein that reproduces the core of the CD4 site interacting with HIV–1 envelope glycoprotein", PNAS 96(23):13091–13096 (1999).

U.S. Appl. No. 60/503,460, filed Sep. 17, 2003 and U.S. Appl. No. 60/604,722, filed Aug. 27, 2004 (see attached copy of WO 2005/028625).

U.S. Appl. No. 10/518, 523, filed Dec. 21, 2004 (U.S. National Phase of WO 2004/009785 see above).

U.S. Appl. No. 10/973,977, filed Oct. 27, 2004.

U.S. Appl. No. 10/973,475, filed Oct. 27, 2004.

U.S. Appl. No. 60/625,720, filed Nov. 8, 2004.

Abaza and Atassi, "Effects of Amino Acid Substitutions Outside an Antigenic Site on Protein Binding to Monoclonal Antibodies of Predetermined Specifcity Obtained by Peptide Immunization: Demonstration with Region 94–100 (Antigenic Site 3) of Myoglobin", Journal of Protein Chemistry 11(5):433–444 (1992).

Fahey et al, "Status of immune–based therapies in HIV infection and AIDS", Clinical and Experimental Immunology 88:1–5 (1992).

Fox, "No winners against AIDS", Bio/Technology 12:128 (1994).

Cohen et al, "Pronounced acute immounosuppresion in vivo mediated by HIV Tat challenge", Proc. Natl. Acad. Sci. USA 96:10842–10847 (1999).

Curse et al, Illustrated Dictionary of Immunology (Boca Raton, Fl. CRC Press, Inc.), p. 309 (1995), QR180.4.C78.

Paul Fundamental Immunology (Philadelphia & New York, Lippincott–Raven Publishers), pp. 250, 1311–1312 and 1387 (1993).

Riffkin et al, "A single amino–acid change between the antigenically different extracellular serine proteases V2 and B2 from *Dichelobactor nodosus*", Gene 167:279–283 (1995).

Zhang et al, "Antibody 17b Binding at the Coreceptor Site Weakens the Kinetics of the Interaction of Envelope Glycoprotein gp120 with CD4", Biochemistry 40:1662–1670 (2001).

Zimsky et al, "Determinants of Human Immunodeficiency Virus Type 1 Resistance of gp41–Derived Inhibitory Peptides", Journal of Virology 7(2):986–993 (1998).

Zhang et al, "Conformational Changes of gp120 in Epitopes near the CCR5 Binding Site Are Induced by CD4 and a CD4 Miniprotein Mimetic", Biochemistry 38:9405–9416 (1999).

Liao et al, "Immunogenicity of Constrained Monoclonal Antibody A32–Human Immunodeficiency Virus (HIV) Env gp120 Complexes Compared to That of Recombinant HIV Type 1 gp120 Envelope Glycoproteins", Journal of Virology 78(10):5270–5278 (2004).

Boots et al, "Anti–Human Immunodeficiency Virus Type 1 Human Monoclonal Antibodies that Bind Discontinous Epitopes in the Viral Glycoproteins Can Identify Mimotopes from Recombinant Phage Peptide Display Libraries", AIDS Research and Human Retroviruses 13(18):1549–1559 (1997).

FIGURE 3

Kinetics and binding affinities of the interactions between pg120 and CD4

| gp120 | $k_a M^{-1} s^{-1}$ (on-rate) | $k_d, s^{-1}$ (off-rate) | $K_d$ M | $t_{1/2}$ min |
|---|---|---|---|---|
| JRFL | $6.0 \times 10^3$ | $8.84 \times 10^{-4}$ | $1.5 \times 10^{-7}$ | 14 |
| DH12 | $4.9 \times 10^3$ | $3.86 \times 10^{-4}$ | $7.8 \times 10^{-8}$ | 30 |
| 89.6 | $4.6 \times 10^3$ | $8.48 \times 10^{-5}$ | $1.8 \times 10^{-8}$ | 136 |

FIGURE 6

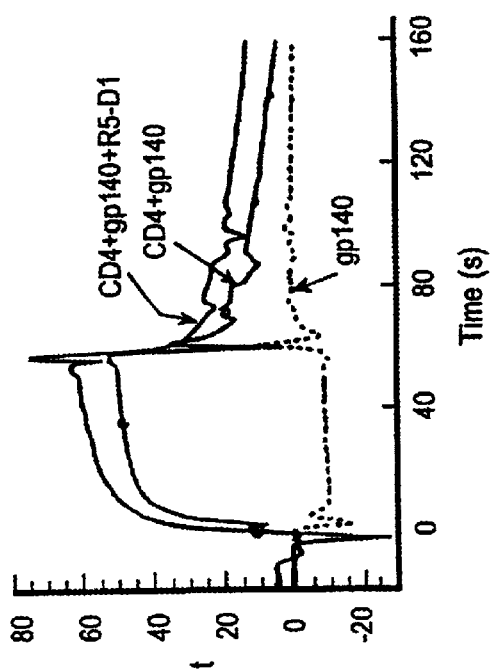
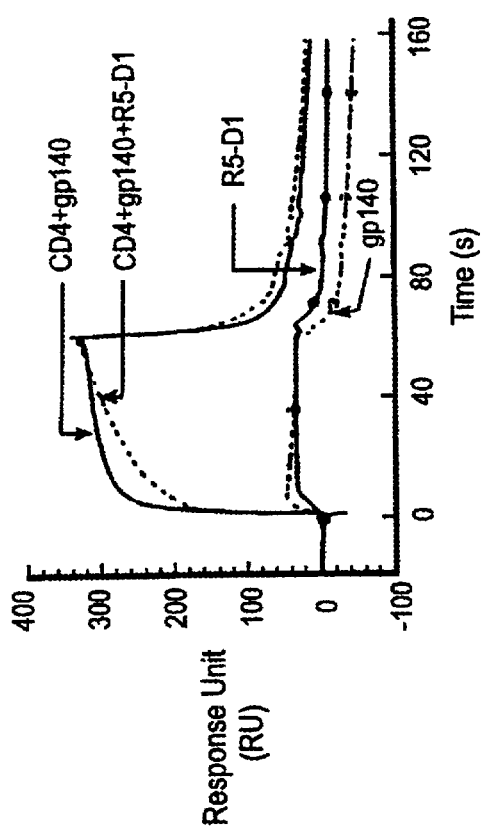
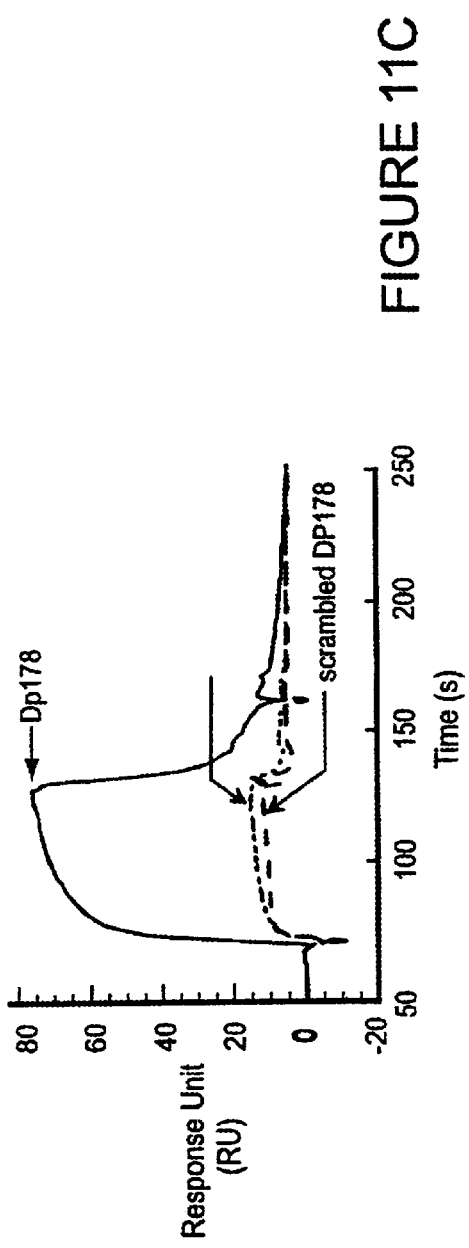
FIGURE 11B
FIGURE 11A
FIGURE 11C

| 89.6 gp140 | $K_a$ $M^{-1}s^{-1}$ | $K_d$ $s^{-1}$ | $K_d$ μM | $t_{1/2}$ s | $R_m$ RU |
|---|---|---|---|---|---|
| DP178 | | | | | |
| CD4+gp140 | $7.9 \times 10^3$ | $5.6 \times 10^{-3}$ | 0.7 | 124 | 320 |
| CD4+gp140+R5-D1 | $3.47 \times 10^3$ | $3.86 \times 10^{-3}$ | 1.1 | 180 | 328 |
| gp140+R5-D1 | nm | nm | nm | nm | 38 |
| gp140 | nm | nm | nm | nm | 35 |
| T694QL | | | | | |
| CD4+gp140 | $6.2 \times 10^3$ | $1.46 \times 10^{-2}$ | 2.4 | 48 | 53 |
| CD4+gp140+R5-D1 | $5.1 \times 10^3$ | $5.3 \times 10^{-3}$ | 1.0 | 131 | 64 |
| gp140+R5-D1 | nm | nm | nm | nm | 0 |
| gp140 | nm | nm | nm | nm | 0 |

FIGURE 11D

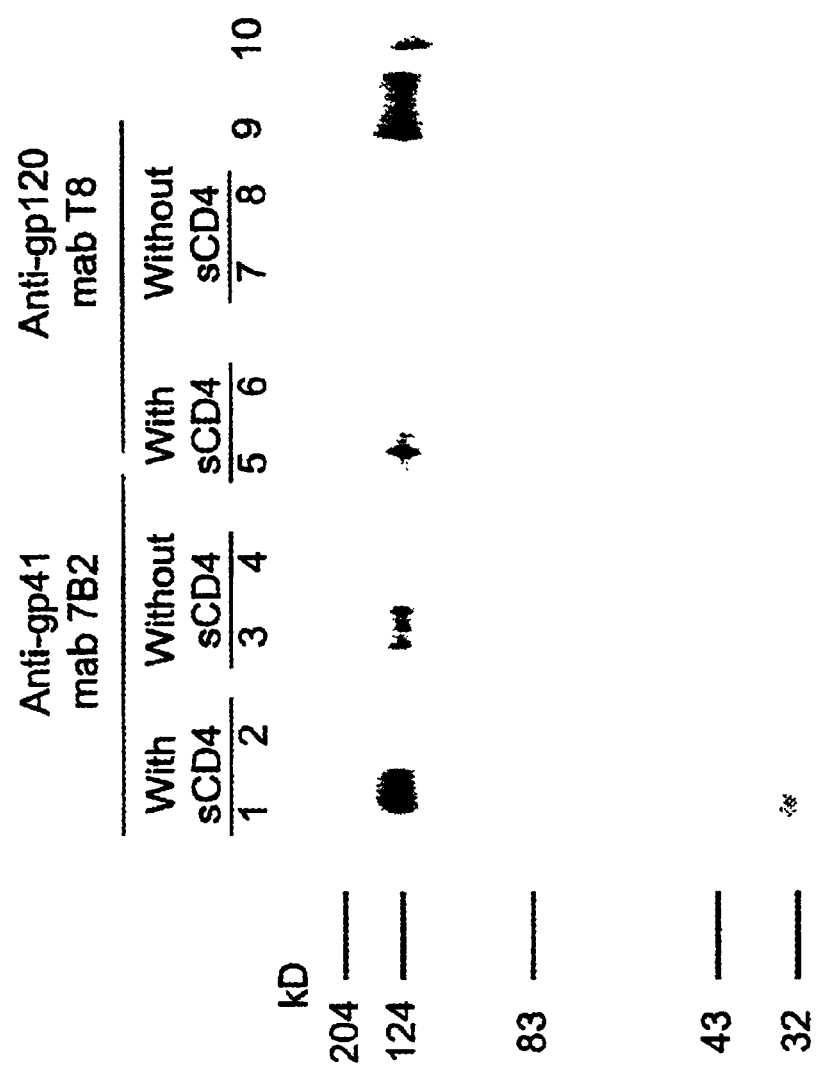

Induced Binding of HR-2 Peptides
to Soluble HIV 89.6 gp140 Envelope

FIGURE 13

|  | $k_{on}$ $M^{-1}s^{-1}$ | $k_{off}$ $s^{-1}$ | $K_d$ µM | $t_{1/2}$ s |
|---|---|---|---|---|
| DP178 | | | | |
| CD4-gp120 | $0.75 \times 10^3$ | $1.5 \times 10^{-3}$ | 2.0 | 462 |
| CD4-gp140 | $0.93 \times 10^3$ | $1.0 \times 10^{-3}$ | 1.1 | 693 |
| T649Q26L | | | | |
| CD4-gp120 | $1.26 \times 10^3$ | $3.2 \times 10^{-3}$ | 2.54 | 217 |
| CD4-gp140 | $0.88 \times 10^3$ | $1.1 \times 10^{-3}$ | 1.20 | 630 |

FIGURE 15E

FIGURE 20

IMMUNOGEN COMPRISING AN HIV ENVELOPE PROTEIN, A LIGAND AND H2 PEPTIDE

This application claims priority from Provisional Application Nos. 60/234,327, filed Sep. 22, 2000, 60/285,173, filed Apr. 23, 2001, 60/323,697, filed Sep. 21, 2001 and 60/323,702, filed Sep. 21, 2001, the entire contents of which are incorporated herein by reference.

This invention was made with Government support under Grant No. A135351 awarded by the National Institutes of Health. The Government has certain rights in the invention.

TECHNICAL FIELD

The present invention relates, in general, to an immunogen and, in particular, to an immunogen for inducing antibodies that neutralize a wide spectrum of HIV primary isolates. The invention also relates to a method of inducing anti-HIV antibodies using such an immunogen.

BACKGROUND

As the HIV epidemic continues to spread world-wide, the need for an effective HIV vaccine remains urgent. A key obstacle to HIV vaccine development is the extraordinary variability of HIV and the rapidity and extent of HIV mutation (Wain-Hobson in The Evolutionary biology of Retroviruses, SSB Morse Ed. Raven Press, NY, pgs 185–209 (1994)).

Myers, Korber and colleagues have analyzed HIV sequences worldwide and divided HIV isolates into groups or clades, and provided a basis for evaluating the evolutionary relationship of individual HIV isolates to each other (Myers et al (Eds), Human Retroviruses and AIDS (1995), Published by Theoretical Biology and Biophysics Group, T-10, Mail Stop K710, Los Alamos National Laboratory, Los Alamos, N. Mex. 87545). The degree of variation in HIV protein regions that contain CTL and T helper epitopes has also recently been analyzed by Korber et al, and sequence variation documented in many CTL and T helper epitopes among HIV isolates (Korber et al (Eds), HIV Molecular Immunology Database (1995), Published by Theoretical Biology and Biophysics Group, Los Alamos National Laboratory, Los Alamos, N. Mex. 87545).

A new level of HIV variation complexity was recently reported by Hahn et al by demonstrating the frequent recombination of HIV among clades (Robinson et al, J. Mol. Evol. 40:245–259 (1995)). These authors suggest that as many as 10% of HIV isolates are mosaics of recombination, suggesting that vaccines based on only one HIV clade will not protect immunized subjects from mosaic HIV isolates (Robinson et al, J. Mol. Evol. 40:245–259 (1995)).

The present invention relates to an immunogen suitable for use in an HIV vaccine. The immunogen will induce broadly cross-reactive neutralizing antibodies in humans and neutralize a wide spectrum of HIV primary isolates.

SUMMARY OF THE INVENTION

The present invention relates to an immunogen for inducing antibodies that neutralize a wide spectrum of HIV primary isolates. The invention also relates to a method of inducing anti-HIV antibodies using such an immunogen.

Objects and advantages of the present invention will be clear from the description that follows.

BRIEF DESCRIPTION OF THE DRAWINGS

FIG. 1 shows CCR5 or CXCR4 co-receptor proteins (or their protein or peptide fragments) and soluble CD4 bound to gp160.

FIG. 2 shows vesicles or liposomes containing CD4, CCR5 (or CXCR4) bound to gp160 in a vesicle, liposome or an inactivated virion.

FIG. 3 shows soluble CD4 and peptides reflective of CCR5 or CXCR4 gp120 binding sites bound to gp160.

FIG. 4 shows B1Acore measurements of binding interactions between soluble gp120 of HIV isolate DH12 and soluble CD4.

FIG. 5 shows binding interactions between HIV 89.6, JRFL, and DH12 soluble gp120 proteins and soluble CD4.

FIG. 6 shows kinetic and binding affinities of the interactions between gp120 and CD4.

FIG. 7 shows binding of soluble CD4 to gp120-expressing membranes from the CHO-wt (HIV-IIIB gp160-expressing) cells.

FIG. 8 shows changes in gp160 and gp140 associated with a structure of gp160 that corresponds with the ability to induce cell fusion.

FIG. 9 shows “freezing” of fusogenic epitopes upon addition of DP-178 or T649 peptides that are parts of the coiled coil region and that, when added to CD4-triggered envelope, result in prevention of fusion.

FIGS. 10A–10D show binding of CD4 and CCR5 N-terminal peptide to HIV 89.6 gp140 oligomers.

FIG. 10A. Overlay of the binding curves of interactions between immobilized CD4 and HIV envelope proteins (89.6 gp120 and gp140). Data show that sCD4 bound to cleaved HIV 89.6 gp140 (c1) and to HIV 89.6 gp120 proteins. The negative control (negative ctrl) was generated by injecting 89.6 gp120 proteins over a CD8 immobilized surface. Compared to HIV JRFL and DH12 gp120 env proteins, HIV 89.6 gp120 env bound to CD4 with a relatively higher affinity ($K_d$=146 nM, 96 nM and 23 nM for JRFL, DH12 and 89.6 env respectively). These differences in $K_d$ were predominantly due to differences in the off-rate ($k_d$=8.8×$10^{-4}$ $s^{-1}$, 4.7×$10^{-4}$ $s^{-1}$, 1.1×$10^{-4}$ $s^{-1}$ for JRFL, DH12 and 89.6 gp120 envelope proteins, respectively).

FIG. 10B. Binding of uncleaved CM235 gp140 (uncl) and IIIB-gp160 (uncl) oligomers to immobilized CD4. Data show that whereas uncleaved IIIB-gp160 (FIG. 10B) oligomers bound poorly to CD4, uncleaved HIV CM235 gp140 (FIG. 10B) oligomers did bind sCD4. The negative control is the same injection of IIIB-gp160 flowing over a surface immobilized with IIIB-gp160 proteins.

FIG. 10C. CD4-gp140 complexes (indicated by arrow) were first formed by injecting soluble 89.6 gp140 oligomers over a CD4-immobilized surface. Then the CCR5 N-terminal peptide (D1) was injected to monitor its binding to CD4-gp140 complexes.

FIG. 10D. An overlay of the binding curves of CCR5 N-terminal peptide, D1, binding to 89.6 gp140 oligomers in the presence and absence of CD4. On a CD4-gp140 complex, the D1 peptide binds with an apparent $K_d$ of 280 nM ($k_a$=9×$10^3$ $M^{-1}$ $s^{-1}$, $k_d$=2.56×$10^{-3}$ $s^{-1}$). In the absence of CD4, the D1 peptide binds constitutively to cleaved gp140 oligomers with a similar on-rate but a faster off-rate ($k_d$=1.01 $s^{-1}$; $K_d$=1 μM). The difference in the steady-state binding of CCR5-D1 peptide in the presence and absence of CD4 is a quantitative effect. To ensure that all gp140 molecules were bound to CD4, cleaved gp140 proteins were captured on a CD4 immobilized sensor surface (RU=530), and soluble 89.6 gp140 proteins were directly immobilized (RU=3300) on an adjacent flow cell of the same sensor chip.

FIGS. 11A–11D show CD4 and CCR5 extracellular domain peptides induce binding of the HR-2 peptides to HIV 89.6 gp140.

FIG. 11A. Binding of HR-2 peptide, DP178 following binding of 89.6 gp140 oligomers to CD4 (solid line), CD4 and CCR5-D1 peptide (broken line), CCR5-D1 peptide (solid circle) and to gp140 oligomers alone (broken lines).

FIG. 11B. Binding of the HR-2 peptide, T649QL to 89.6 gp140 oligomers (broken line), CD4-gp140 complex (open circle) and to CD4-gp140-D1 complex (solid line). 89.6 gp140 proteins and CCR5-D1 peptide were sequentially injected over a sCD4 immobilized surface (see FIG. 10C).

FIG. 11C. Binding of HR-2 peptides, DP178 and a control scrambled DP178 peptides to CD4-89.6 gp140 complexes.

FIG. 11D. Kinetics data for the binding of HR-2 peptides, DP178 and T649QL to 89.6 gp140 after induction with CD4 and the CCR5-D1 peptide. Rm refers to the RU bound at steady-state during the injection of the same conc of HR-2 peptides (5 mM) over the indicated gp140 complexes. nm=rate constants could not be measured due to extremely low affinity binding of HR-2 peptides to gp140 proteins.

FIG. 12 shows immunoprecipitation by HR-2 peptide and western blot analysis of 89.6 gp140 envelope proteins. Biotinylated HR-2 peptide, DP178 constitutively immunoprecipitated both cleaved gp41 and uncleaved gp140 proteins. The level of immunoprecipitated gp140 and gp41 was augmented by sCD4. HIV 89.6 gp140 proteins were incubated with 2.5 μg of biotinylated DP178 in the presence (Lanes 1 and 5) or absence (Lanes 3 and 7) of sCD4 (2 μg). As controls, HIV 89.6 gp140 proteins were also incubated with 2.5 μg of biotinylated scrambled DP178 peptide in the presence (Lanes 2 and 6) or absence (Lanes 4 and 8) of sCD4 (2 μg). Lane 9 shows gp140 and gp41 within the gp140 preparation immunoblotted with mab 7B2 (anti-gp41), while Lane 10 shows gp120 within the gp140 preparation reactive with mab T8 (anti-gp120).

FIG. 13 shows the induced binding of HR-2 peptides to soluble HIV 89.6 gp140 envelope.

Figure 14A:
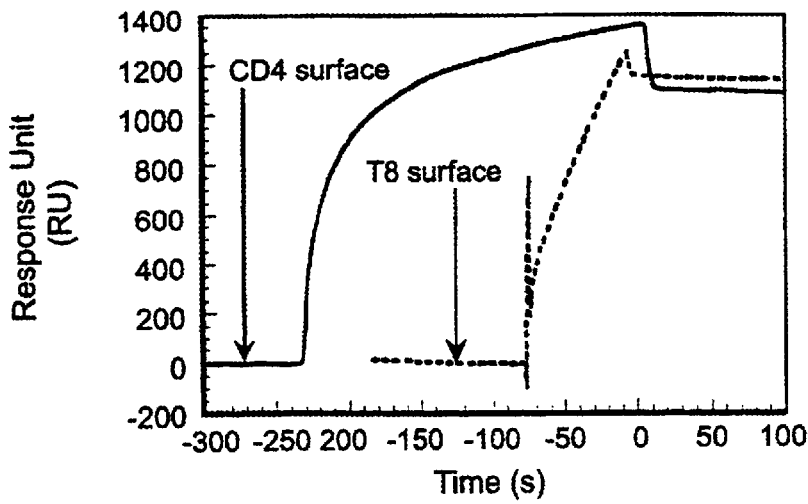
Figure 14B:
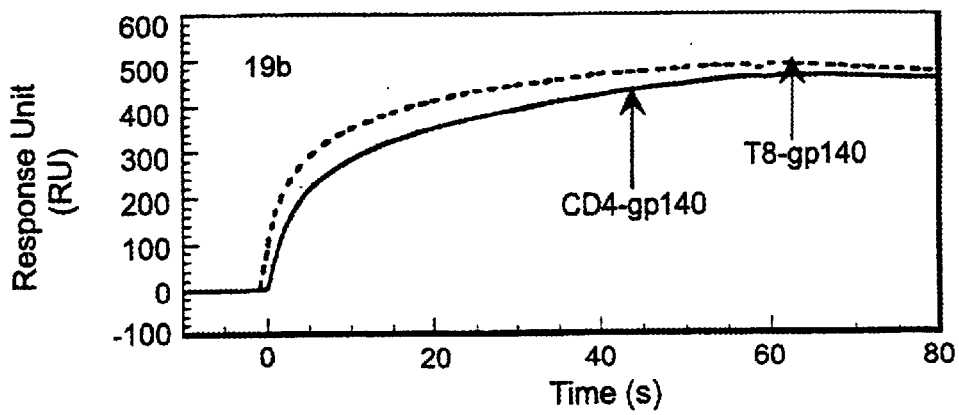
Figure 14C:
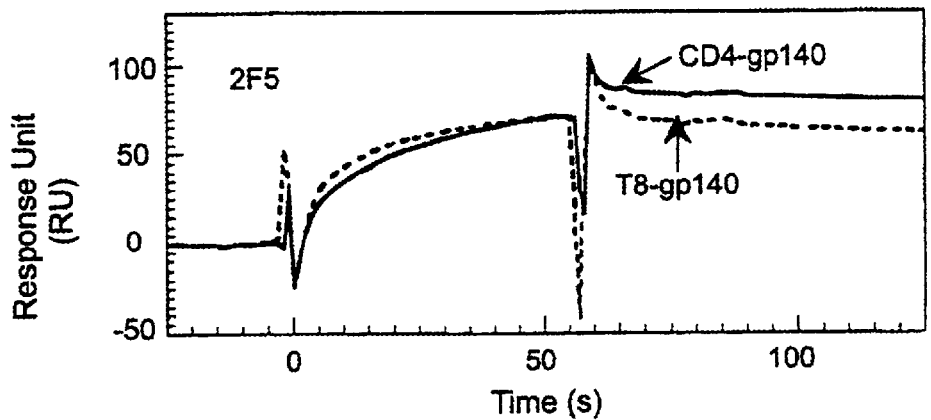
Figure 14D:
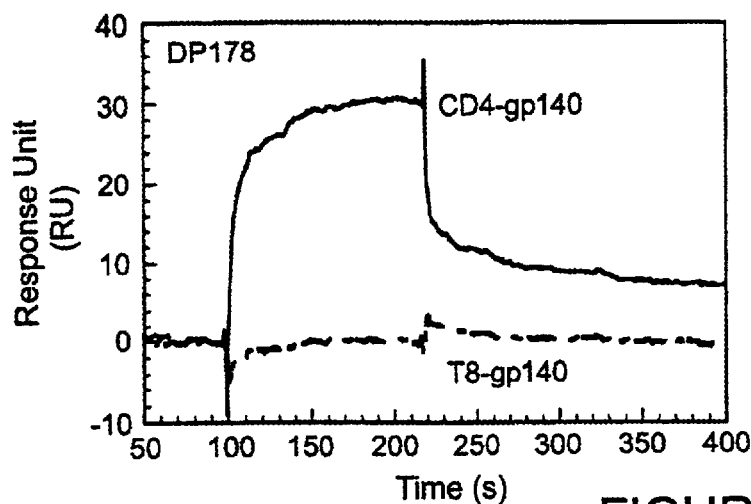
Figure 14E:
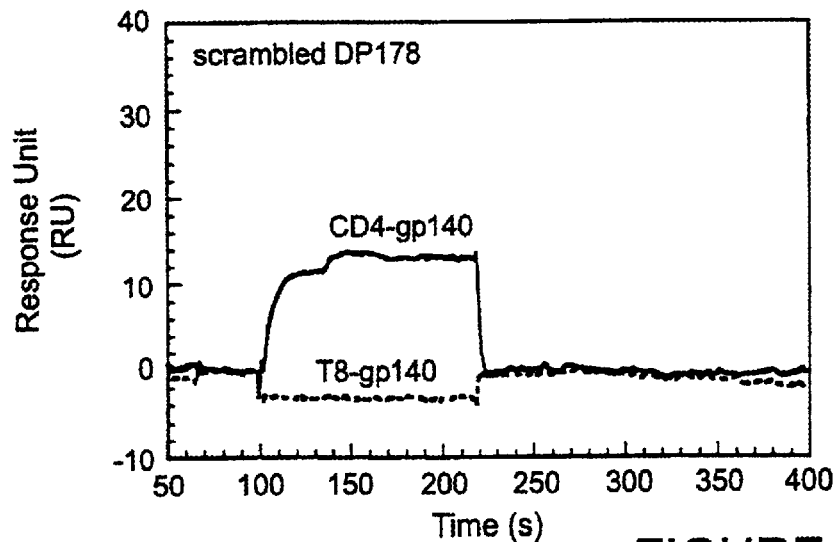
Figure 14F:
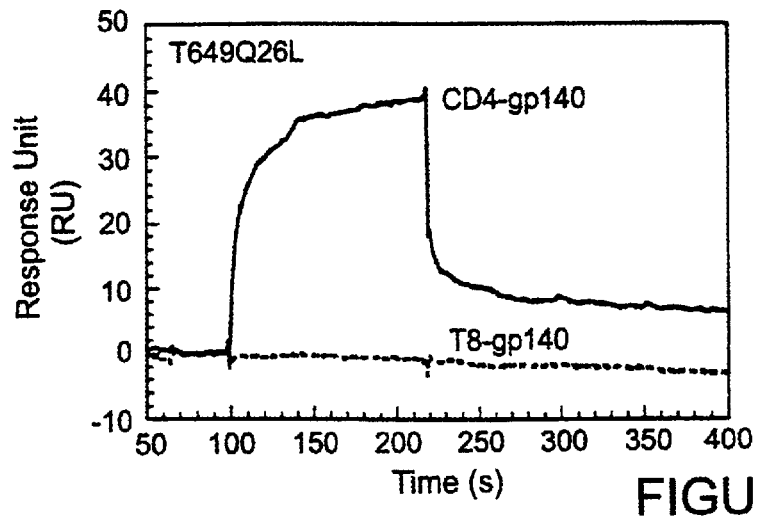

FIGS. 14A–14F show induction of HR-2 peptide binding to 89.6 gp140 by soluble CD4. FIG. 14A. Capture of soluble 89.6 gp140 over a CD4 (solid lines) and T8 (broken lines) immobilized surface. Roughly 3000 to 5000 RU of sCD4 and T8 mab were immobilized on a CM5 sensor chip. Soluble 89.6 gp140 proteins were then captured to the same level on both surfaces and are labeled CD4-gp140 and T8-gp140 respectively. FIGS. 14B and 14C. Binding of the 19b (FIG. 14B) and 2F5 (FIG. 14C) antibodies to CD4-gp140 (solid line) and T8-gp140 (broken line) complexes. After stabilization of gp140 capture, either the 19b (anti-gp120 V3) or 2F5 (anti-gp41) antibodies (300 μg/ml) were injected to assess the relative amounts of gp120 and gp41 on both surfaces. FIGS. 14D–14F. Binding of HR-2 peptide, DP178 (FIGS. 14D), scrambled DP178 (FIG. 14E) and T649Q26L (FIG. 14E) to CD4-gp140 (solid line) or T8-gp140 (broken line) surfaces. 50 μg/ml of each HR-2 peptide was injected at 30 μl/min over both CD4 and T8 surfaces.

Figure 15B:
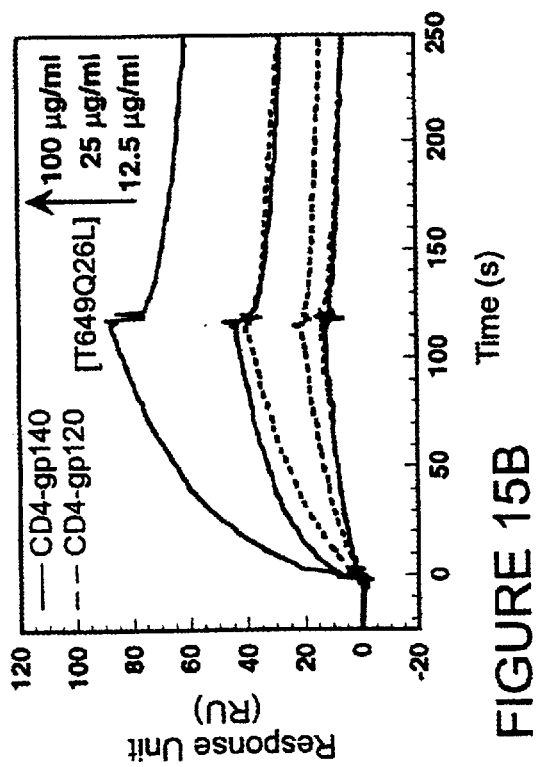
Figure 15D:
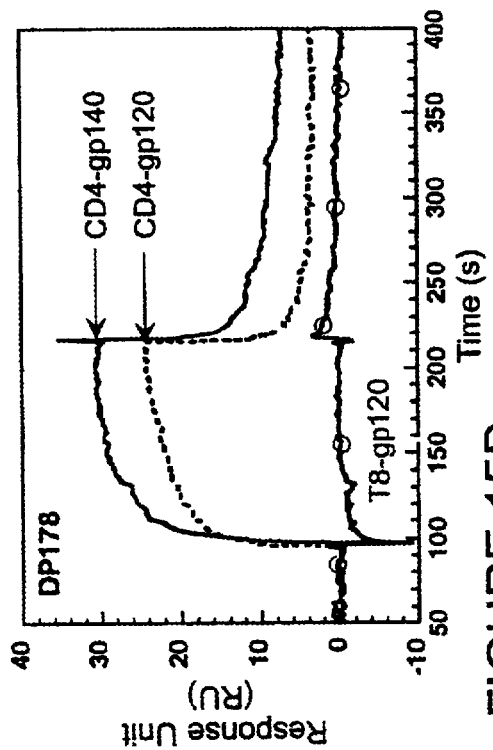
Figure 15A:
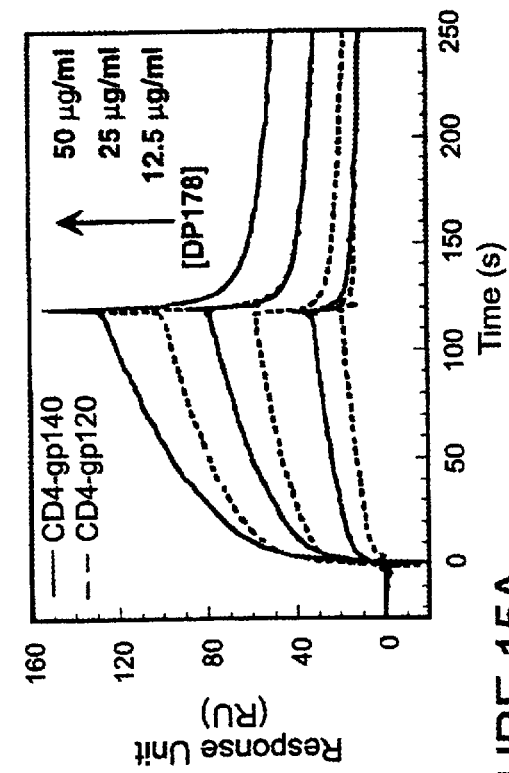
Figure 15C:
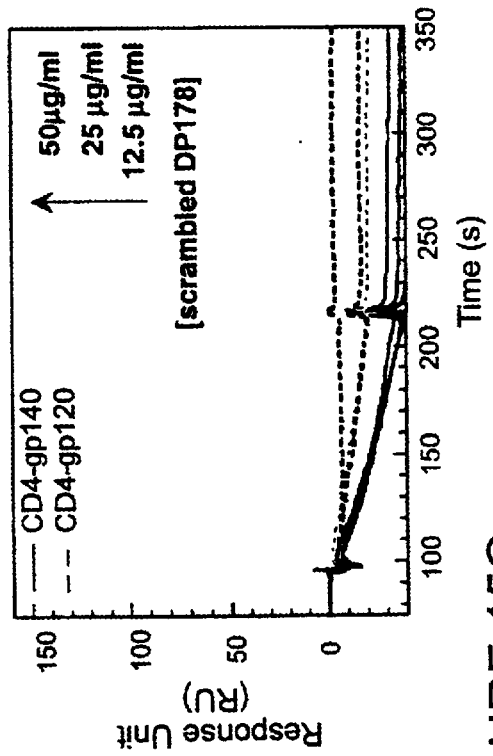

FIGS. 15A–15E show binding interactions of HR-2 peptides with CD4-gp140 and CD4-gp120 complexes. FIGS. 15A and 15B. Overlay of the binding curves showing the interactions between HR-2 peptides, DP178 (FIG. 15A) and T649Q26L (FIG. 15B), and CD4-gp120 (broken lines) and CD4-gp140 (solid lines). FIGS. 15A and 15B show the titration of the HR-2 peptide DP178 and T649Q26L between 12.5 to 100 μg/ml over CD4-gp140 (solid lines) and CD4-gp120 (broken lines) surfaces. FIG. 15C. There was no binding of scrambled DP178 HR-2 peptide to either CD4-gp140 or T8-gp140. FIG. 15D. CD4 induced HR-2 peptide binding to gp120 envelope proteins. There was no specific binding of HR-2 peptides to the T8-gp120 complex, while the sCD4-gp120 and sCD4-gp140 surfaces did stably bind HR-2 peptides. Compared to CD4-gp120, higher binding was observed with CD4-gp140. Table in FIG. 15E shows the binding rate constants and dissociation constants for the HR-2 peptides and CD4-gp120 and CD4-gp140 complexes. Data are representative of 2 separate experiments. HR-2 peptides were injected at 30 μl/min simultaneously over a blank, sCD4 and a sCD4-gp120 or sCD4-gp140 surfaces. The curves presented show specific binding to CD4-gp120 or CD4-gp140 and were derived after subtraction of binding signals from blank and sCD4 surfaces.

Figure 16A:
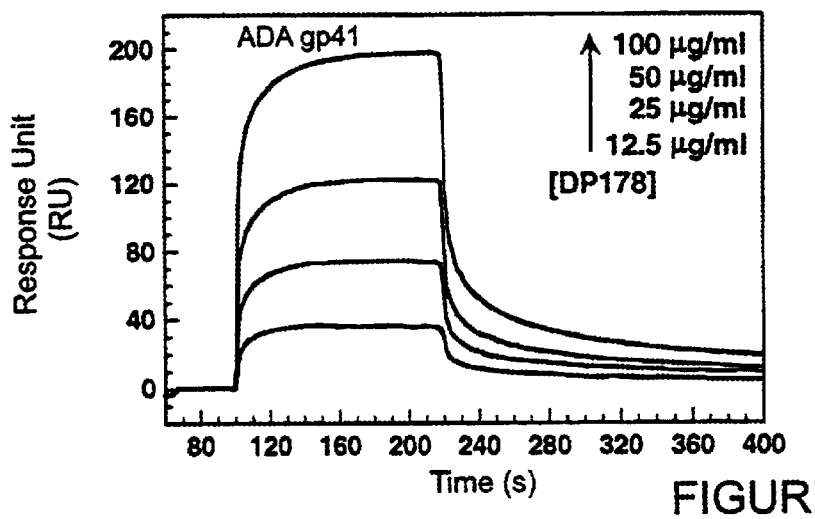
Figure 16B:
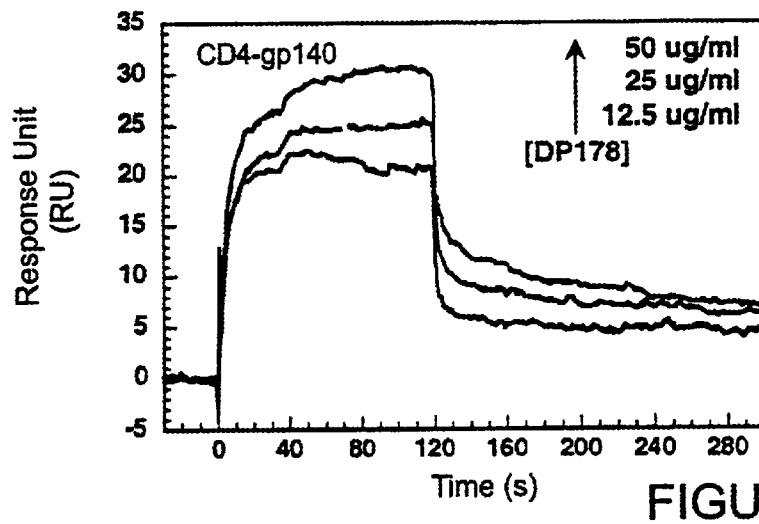
Figure 16C:
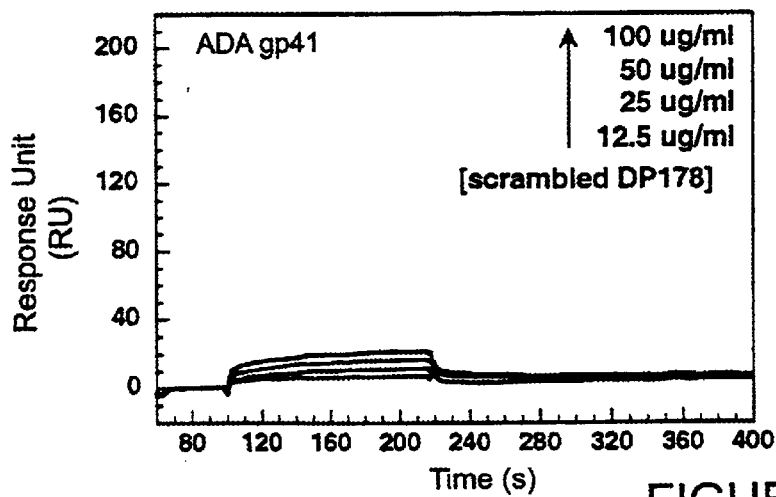
Figure 16D:
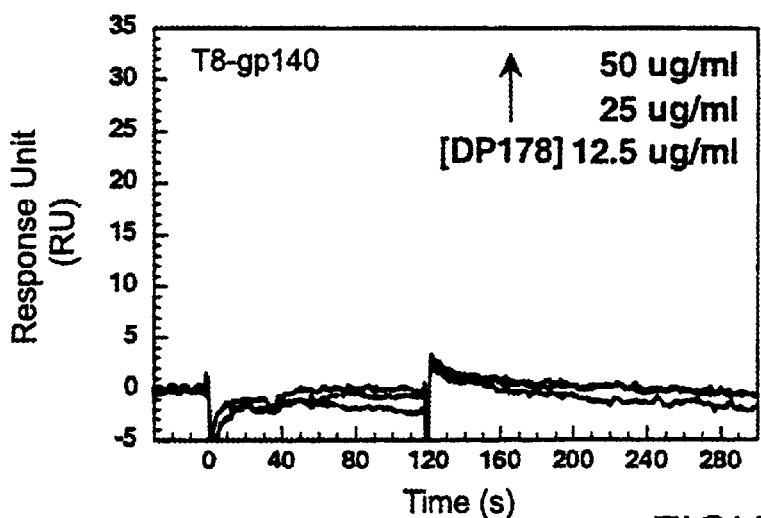
Figure 16E:
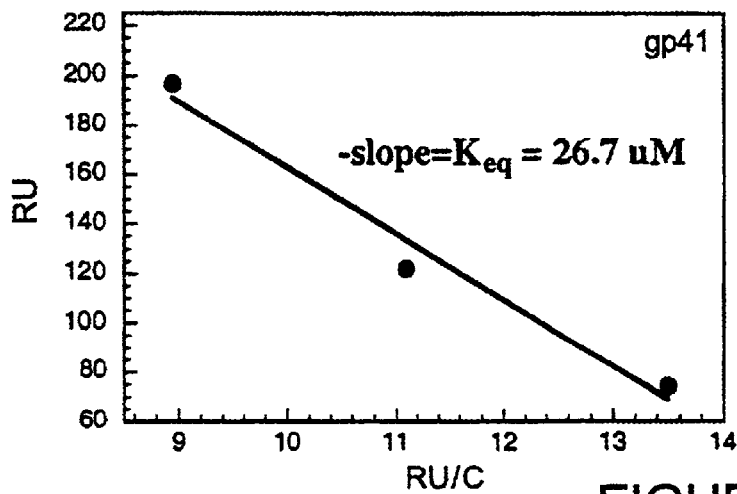
Figure 16F:
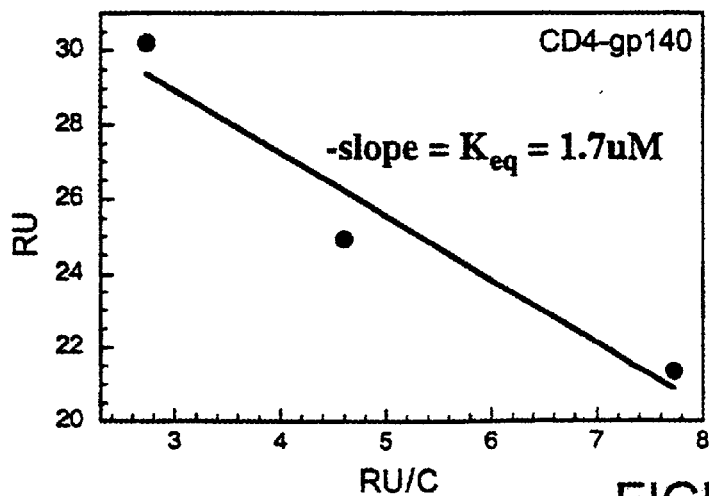

FIGS. 16A–16F show constitutive binding of HR-2 peptides to immobilized gp41 and CD4 induced binding to gp140. FIGS. 16A and 16B. Binding of DP178 (12.5 to 100 μg/ml) to immobilized ADA gp41 and CD4-gp140 (FIG. 16B) surfaces. FIGS. 16C and 16D. Binding of scrambled DP178 (12.5 to 100 μg/ml, FIG. 16D) to immobilized ADA gp41 and the binding of HR-2 peptide, DP178 (12.5 to 50 μg/ml) to T8-gp140 surfaces. FIGS. 16E and 16F. Scatchard plots of RU vs RU/C for DP178 binding to gp41 (FIG. 16E) and to CD4-gp140 (FIG. 16F). Data are representative of 2 separate experiments.

Figure 17A:
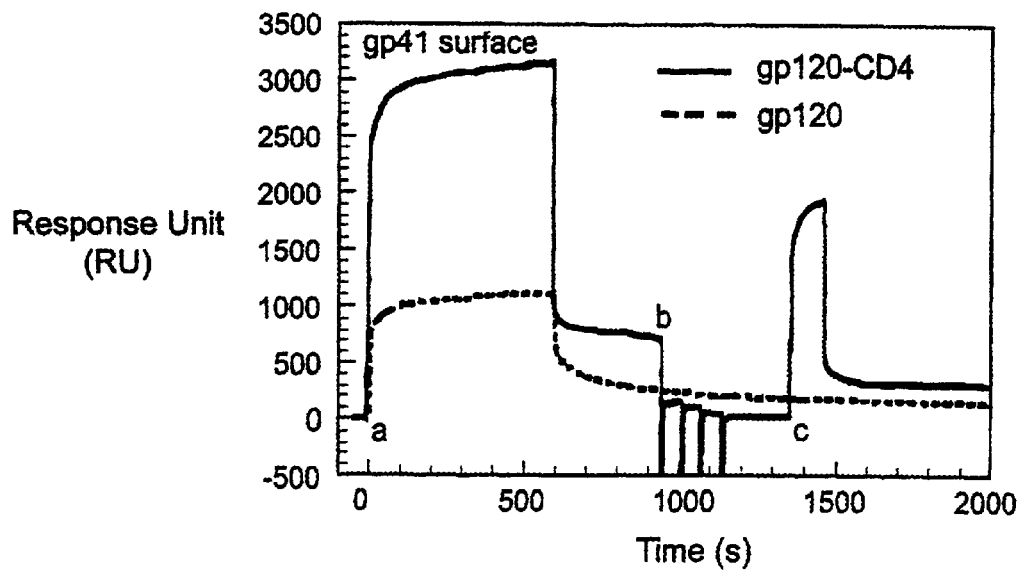
Figure 17B:
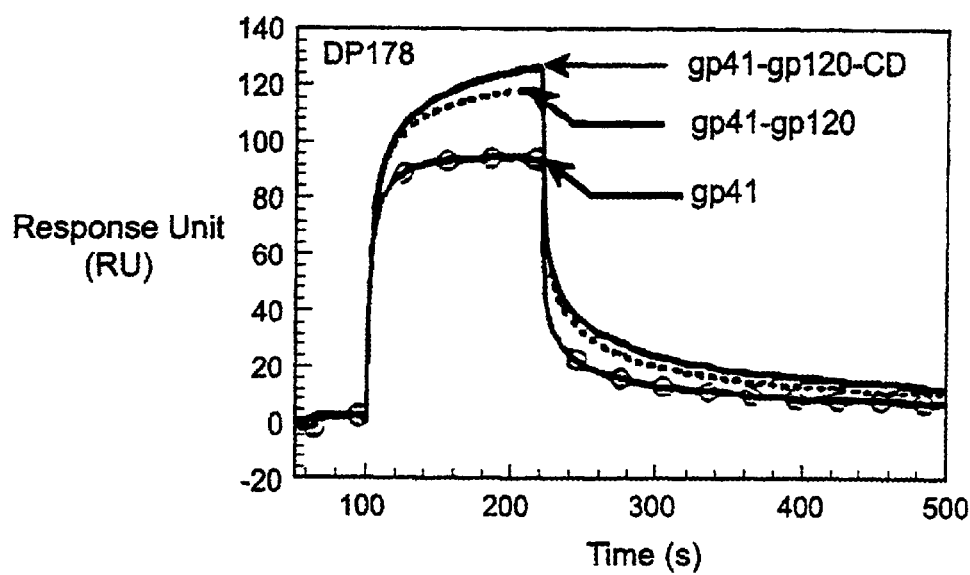

FIGS. 17A and 17B show induction of HR-2 peptide binding to gp120-gp41 complex. Binding of HR-2 peptide DP178 (50 μg/ml) to immobilized gp41, gp41-gp120 and gp41-gp120-CD4 complexes. Compared to gp41 surface, higher binding of DP178 is observed on gp41-gp120 and gp41-gp120-CD4 surfaces. Soluble 89.6 gp120 (100 μg/ml) or a gp120-CD4 mixture (gp120 pre-incubated with 0.3 mg/ml of CD4 for 30 min) was injected at 5 μl/min for 10 min over a sensor surface immobilized with ADA gp41. At the end of the injections, wash buffer (PBS) was allowed to flow until the surface was stable with no baseline drift. Roughly 300 RU of gp120 and 850 RU of gp120-CD4 formed stable complexes with the immobilized gp41 surface. The gp120-CD4 binding was subsequently reduced to about 325 RU (to be rougly equivalent to gp41-gp120 surface) with short injections of a regeneration buffer (10 mM glycine-HCl, pH 2.0), followed by an injection of gp120-CD4 mixture. Thus both surfaces were stable and had equivalent amount of associated gp120 or gp120-CD4.

Figure 18:
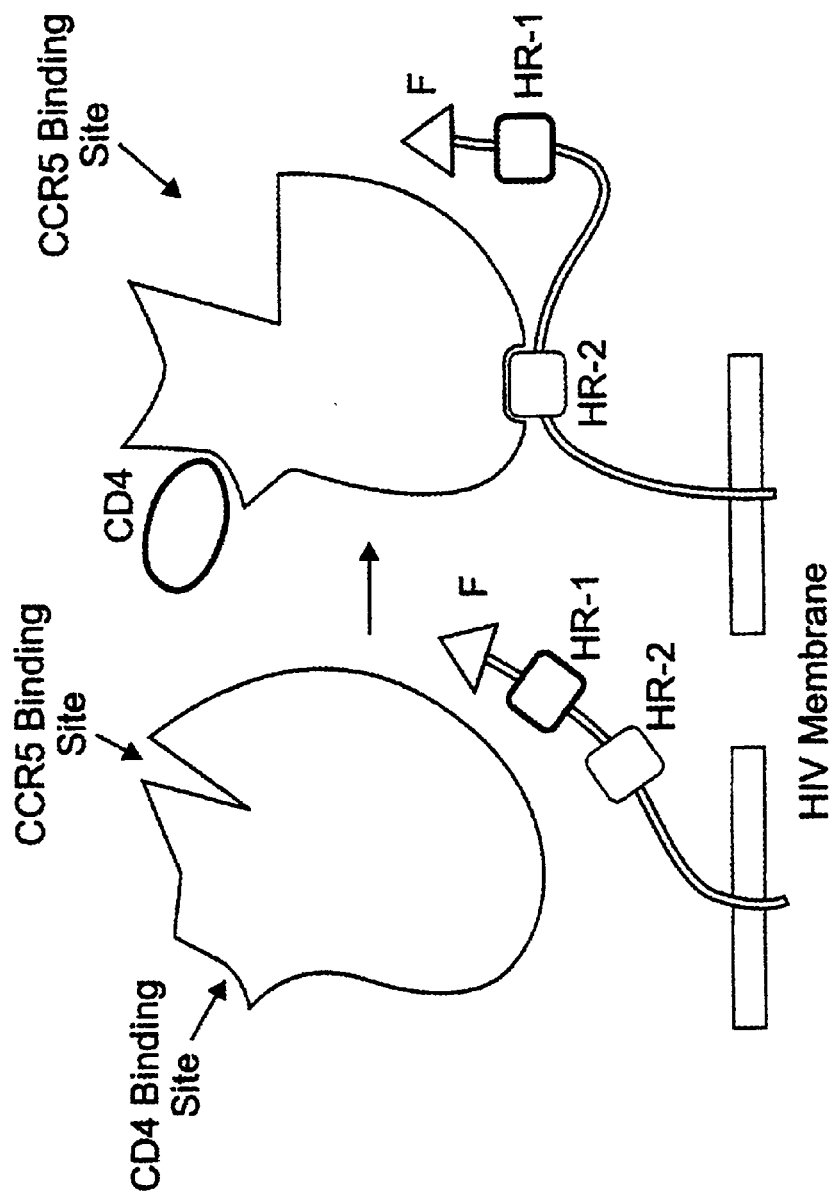

FIG. 18. Soluble CD4 binding to HIV gp120 non-covalently linked to gp41 results in binding of HR-2 to gp120 and upregulation of gp41-gp120 association. An immunogen is cross-linked CD4-gp120-gp41 in soluble form.

Figure 19:
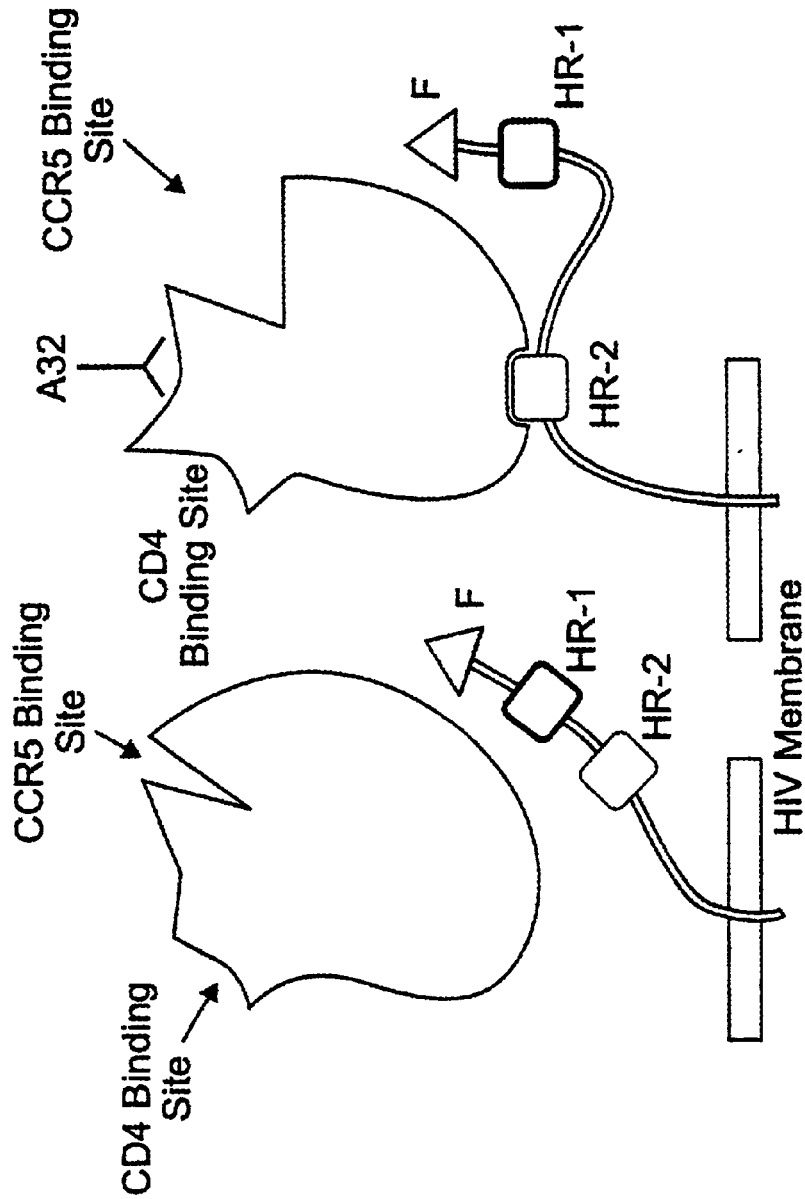

FIG. 19. A32 binding to HIV gp120 non-covalently linked to gp41 results in binding of HR-2 to gp120 and upregulation of gp41-gp120 association. An immunogen is cross-linked A32 (whole Ig)-gp120-gp41 in soluble form or A32 (Fab or Fab2)-gp120-gp41 in soluble form.

Figure 20:
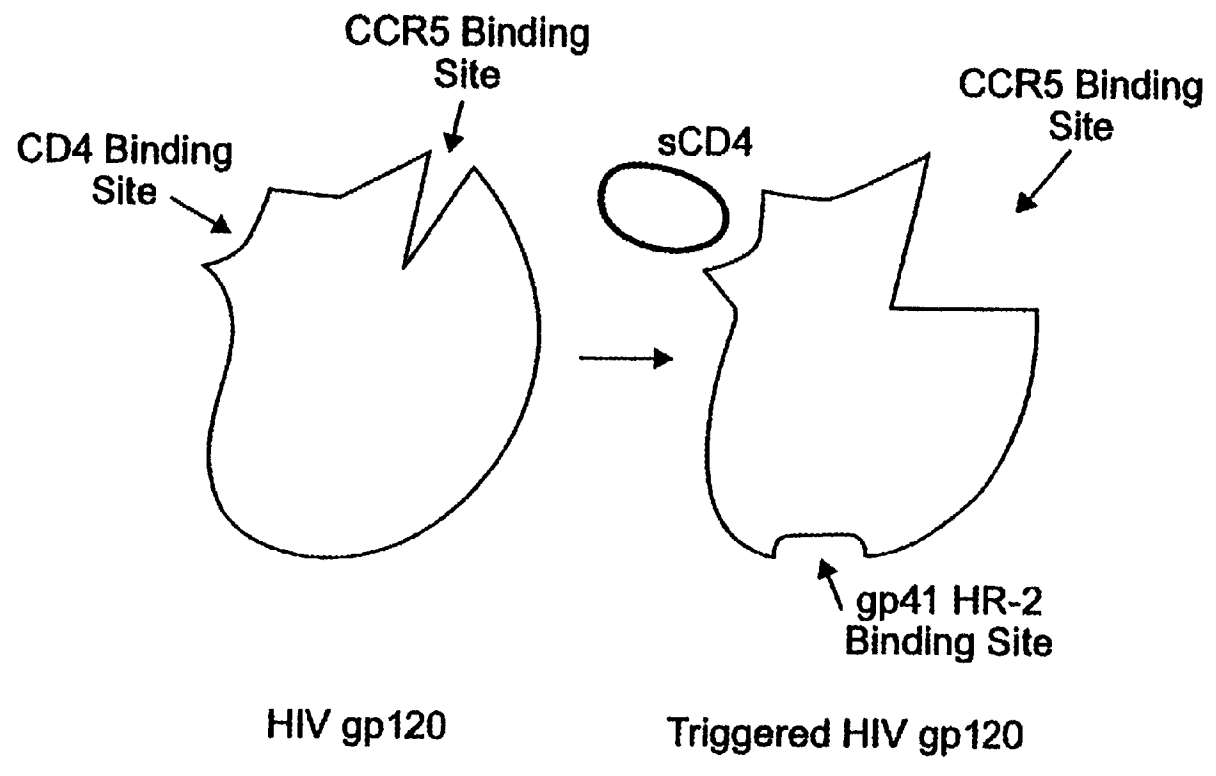

FIG. 20. Soluble CD4 binding to soluble gp120 results in exposure of the CCR5 binding site, and the gp41 HR-2 binding site.

Figure 21:
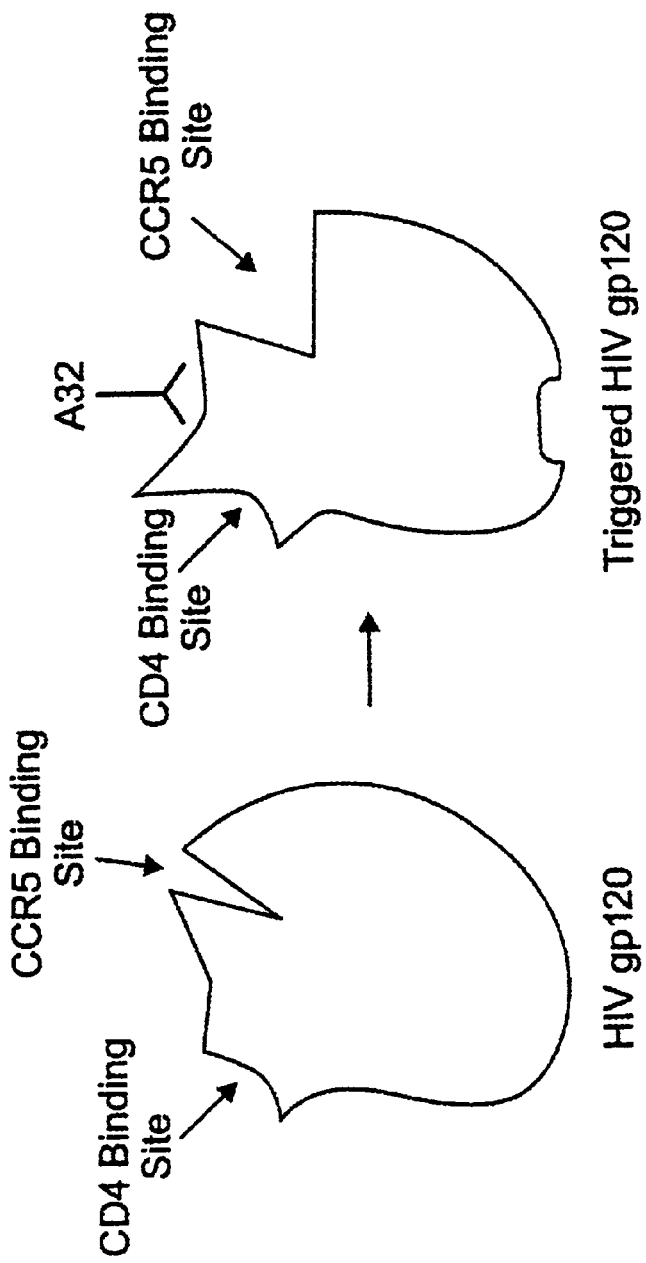

FIG. 21. A32 mab binding to soluble HIV gp120 results in exposure of the CD4 binding site and the CCR5 binding site.

Figure 22:
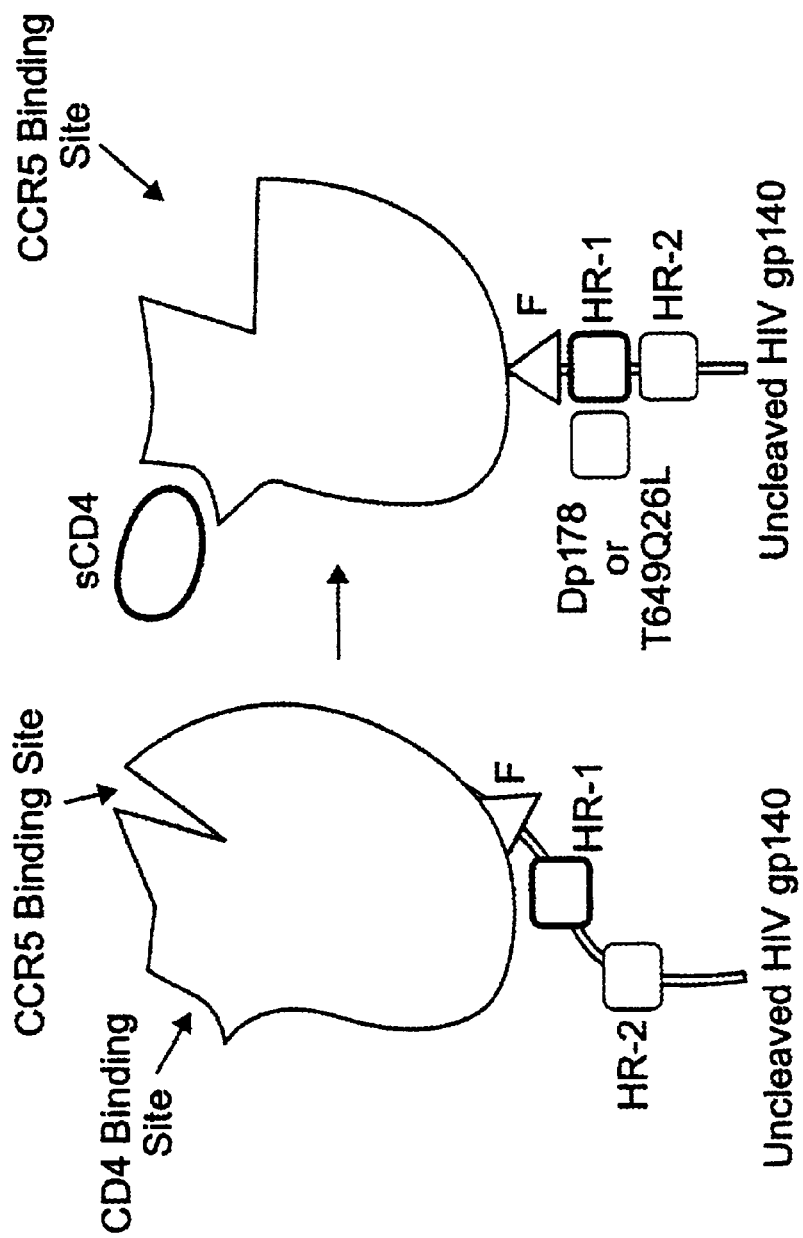

FIG. 22. Soluble CD4 binding to soluble uncleaved HIV gp140 upregulates HR-2 binding to HR-1 in gp41, and exposes the CCR5 binding site. An immunogen is crosslinked CD4-gp140 with or without DP178 or T649Q26L bound.

Figure 23:
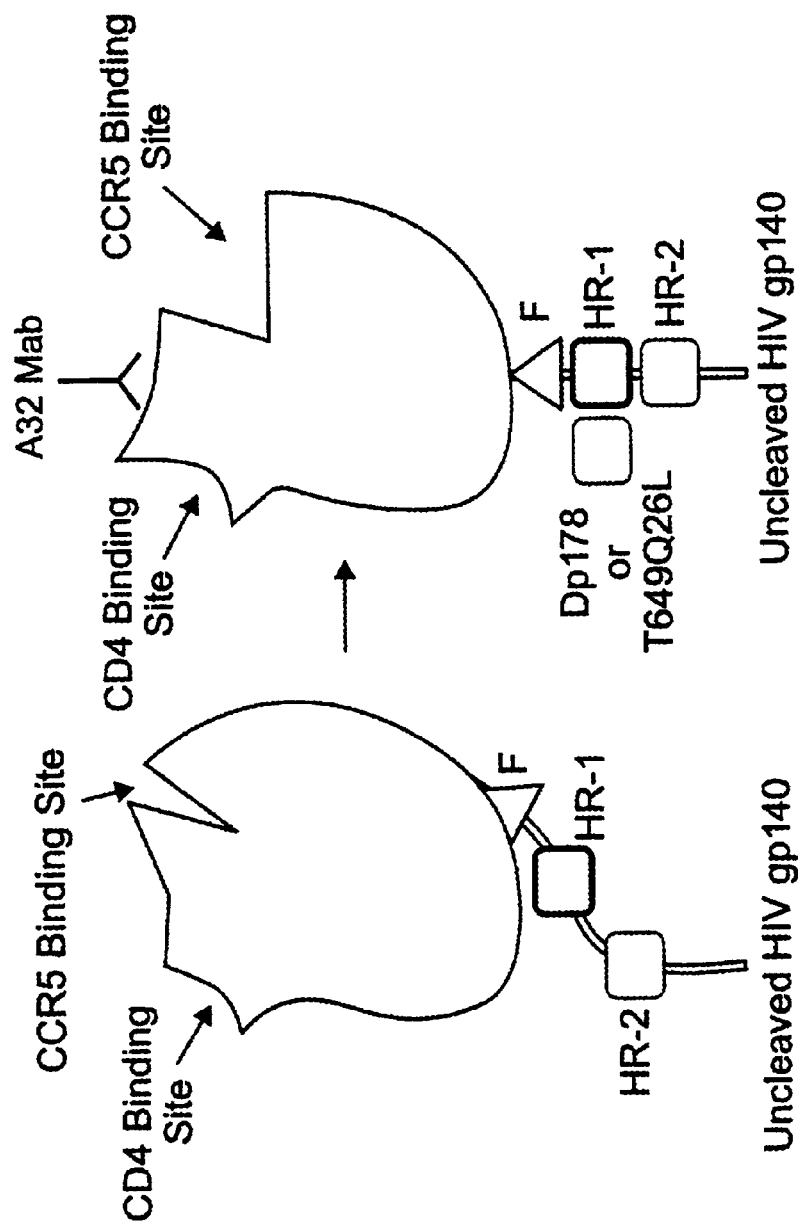

FIG. 23. Mab A32 binding to soluble uncleaved HIV gp140 upregulates HR-2 binding to HR-1 in gp41, and exposes the CCR5 binding site. An immunogen is crosslinked A32 or a fragment thereof—gp140 with or without DP178 or T649Q26L bound to gp41 or elsewhere in the complex.

Figure 24:
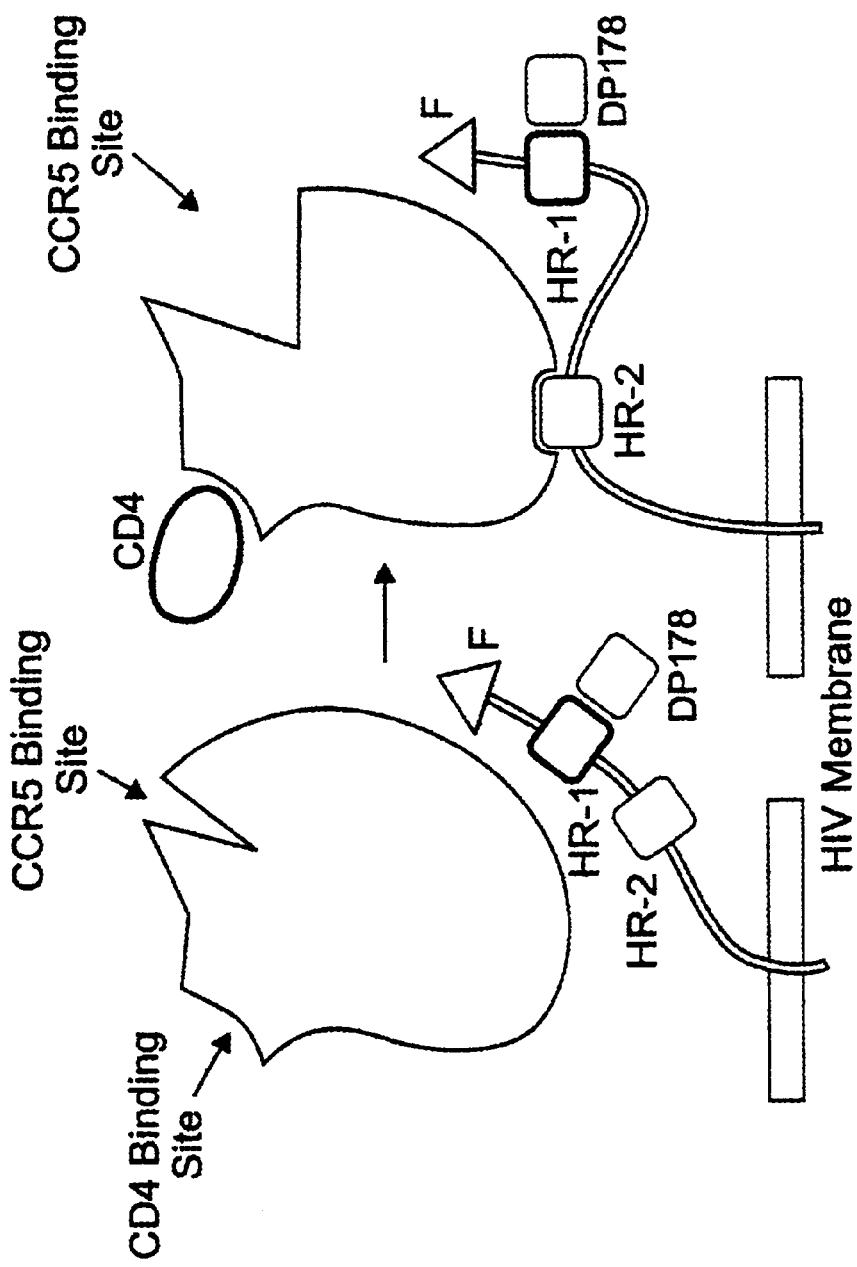

FIG. 24. Soluble CD4 binding to HIV gp120 non-covalently linked to gp41 results in binding of HR-2 to gp120 and upregulation of gp41-gp120 association. An immunogen is cross-linked CD4-gp120-gp41 in soluble form, with HR-2 peptides bound to HR-1.

Figure 25:
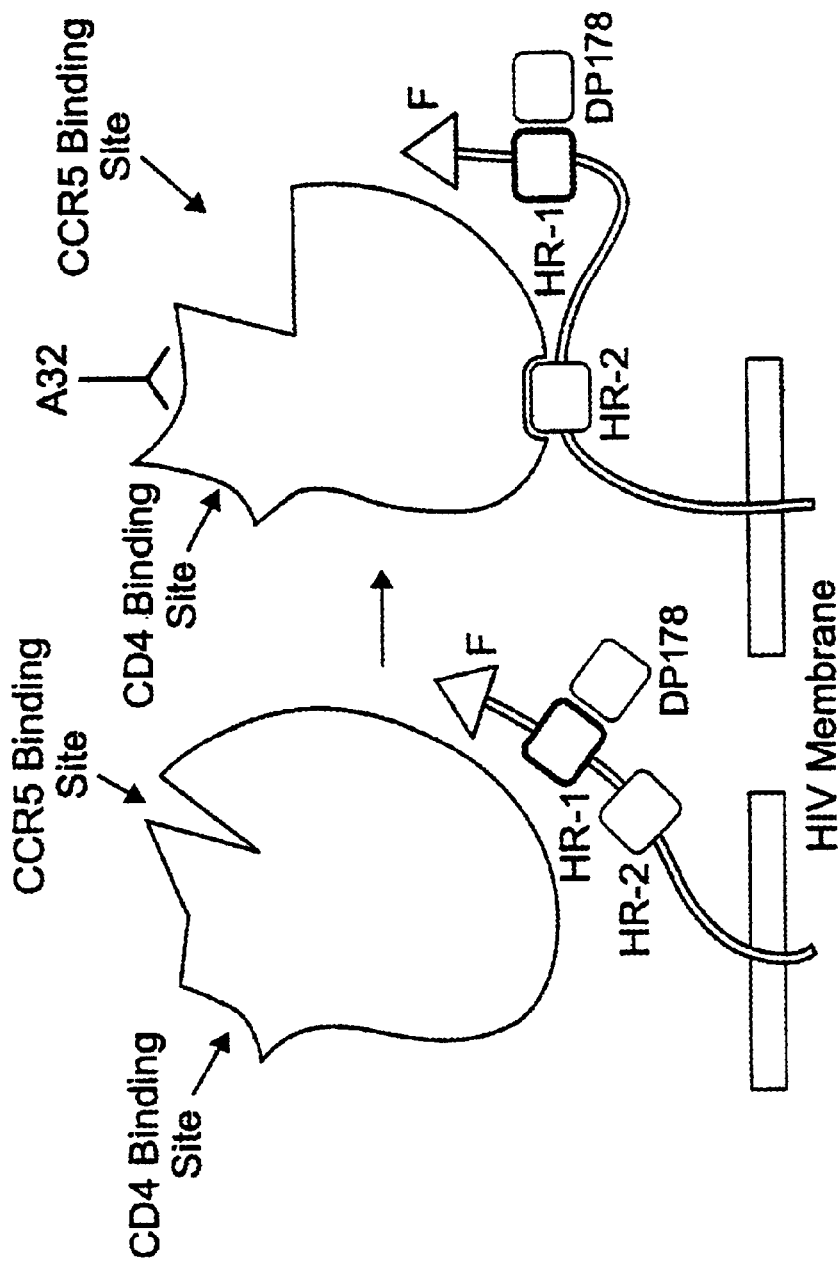

FIG. 25. A32 binding to HIV gp120 non-covalently linked to gp41 results in binding of HR-2 to gp120 and upregulation of gp41-gp120 association. An immunogen is cross-linked A32 (whole Ig)-gp120-gp41 in soluble form or A32 (Fab or Fab2)-gp120-gp41 in soluble form, with HR-2 peptide bound to HR-1 or elsewhere in the complex.

Figure 26:
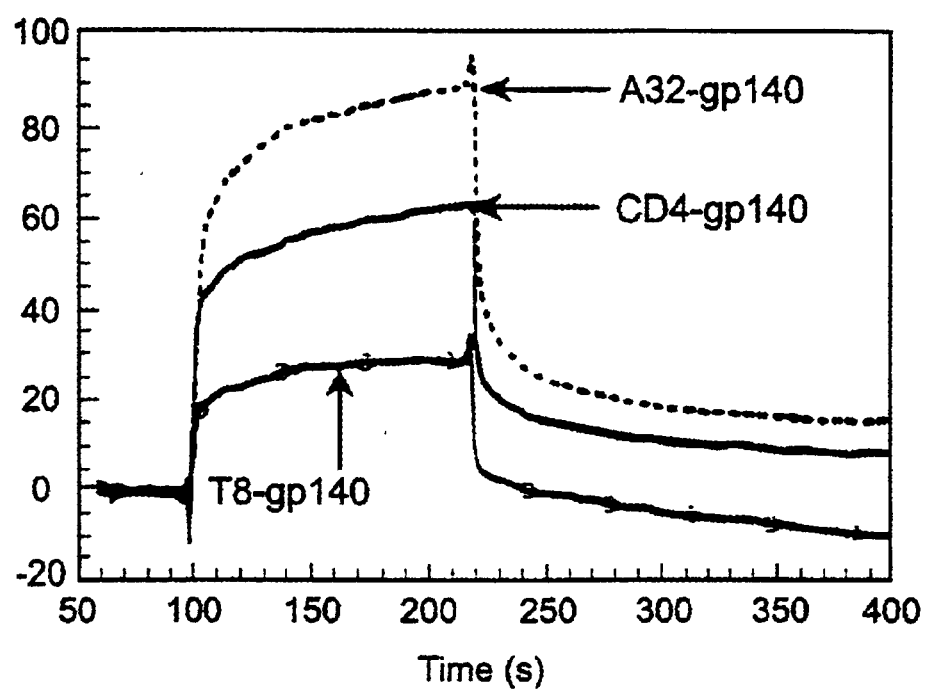

FIG. 26. Induction of HR-2 peptide binding to HIV 89.6 gp140 by soluble CD4. Soluble 89.6 gp140 proteins were captured to the same level on all three surfaces and are labeled CD4-gp140, T8-gp140 and A32-gp140. Figure shows binding of HR-2 peptide DP178 to T8-gp140 (circle), CD4-gp140 (solid line) and A32-gp140 (broken line) complexes. 50 µg/ml of HR-2 peptide was injected at 30 µl/min over A32, CD4 and T8 surfaces. Only specific binding, after bulk responses and non-specific binding of HR-2 peptides to sCD4, T8 and A32 surfaces were subtracted, are shown.

DETAILED DESCRIPTION OF THE INVENTION

The present invention relates to an immunogen that induces broadly reactive neutralizing antibodies that are necessary for an effective AIDS vaccine. In one embodiment, the immunogen comprises a cleaved or uncleaved gp140 or gp160 HIV envelope protein that has been "activated" to expose intermediate conformations of conserved neutralization epitopes that normally are only transiently or less well exposed on the surface of the HIV virion. The immunogen is a "frozen" triggered form of HIV envelope that makes available specific epitopes for presentation to B lymphocytes. The result of this epitope presentation is the production of antibodies that broadly neutralize HIV.

The concept of a fusion intermediate immunogen is consistent with observations that the gp41 HR-2 region peptide, DP178, can capture an uncoiled conformation of gp41 (Furata et al, Nature Struct. Biol. 5:276 (1998)), and that formalin-fixed HIV-infected cells can generate broadly neutralizing antibodies (LaCasse et al, Science 283:357 (1997)). Recently a monoclonal antibody against the coiled-coil region bound to a conformational determinant of gp41 in HR1 and HR2 regions of the coiled-coil gp41 structure, but did not neutralize HIV (Jiang et al, J. Virol. 10213 (1998)). However, this latter study proved that the coiled-coil region is available for antibody to bind if the correct antibody is generated.

Conserved neutralization sites on the HIV envelope can be on two regions; they can be on gp41 and they can be on gp120.

The regions and conformations of gp41 that are exposed during gp140 or gp160 "triggering" ("activation") can be expected to be conserved since: i) the amino acid sequences of the coiled-coil region are conserved and ii) the function of the fusogenic envelope complex is conserved and essential for virus pathogenicity. This conservation is key to the production of broadly neutralizing anti-HIV antibodies.

Figure 2:
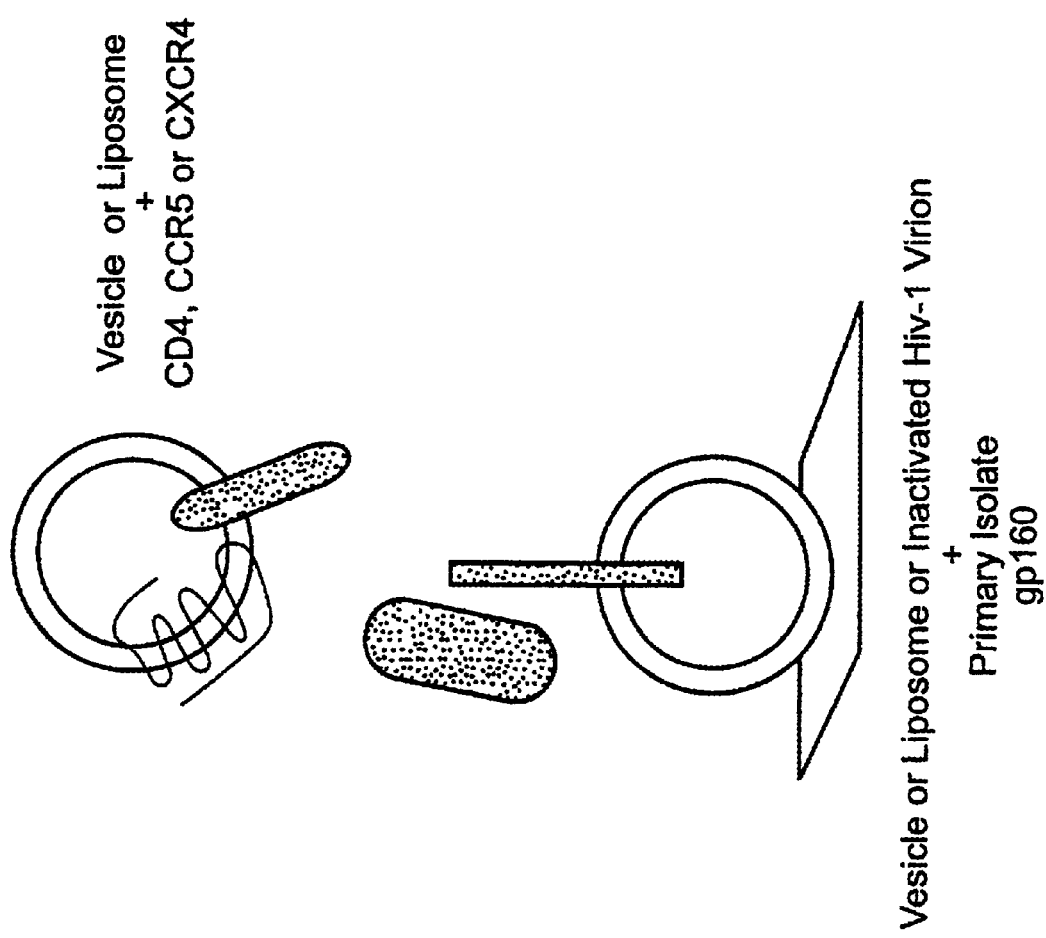
Figure 3:
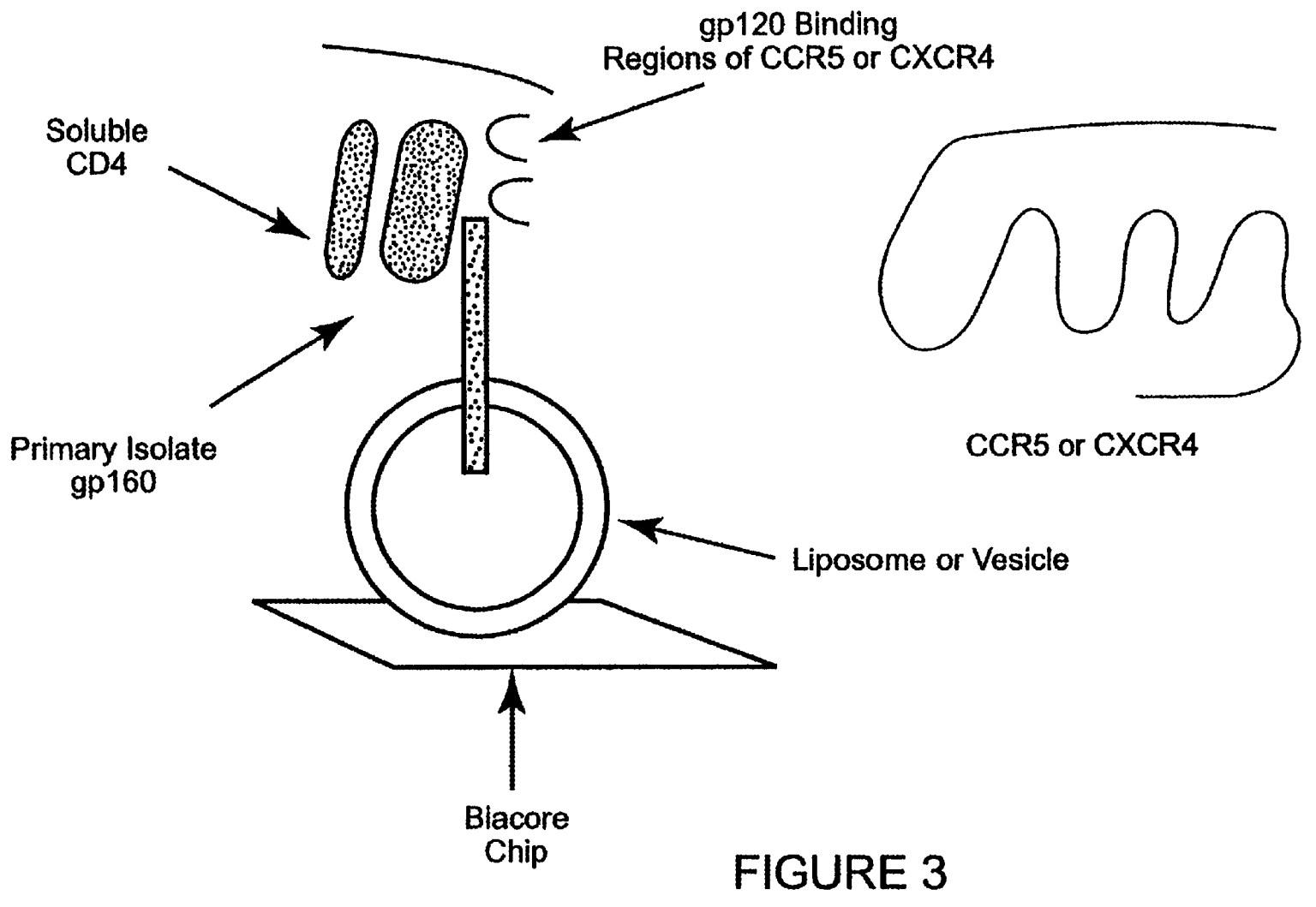
Figure 8:
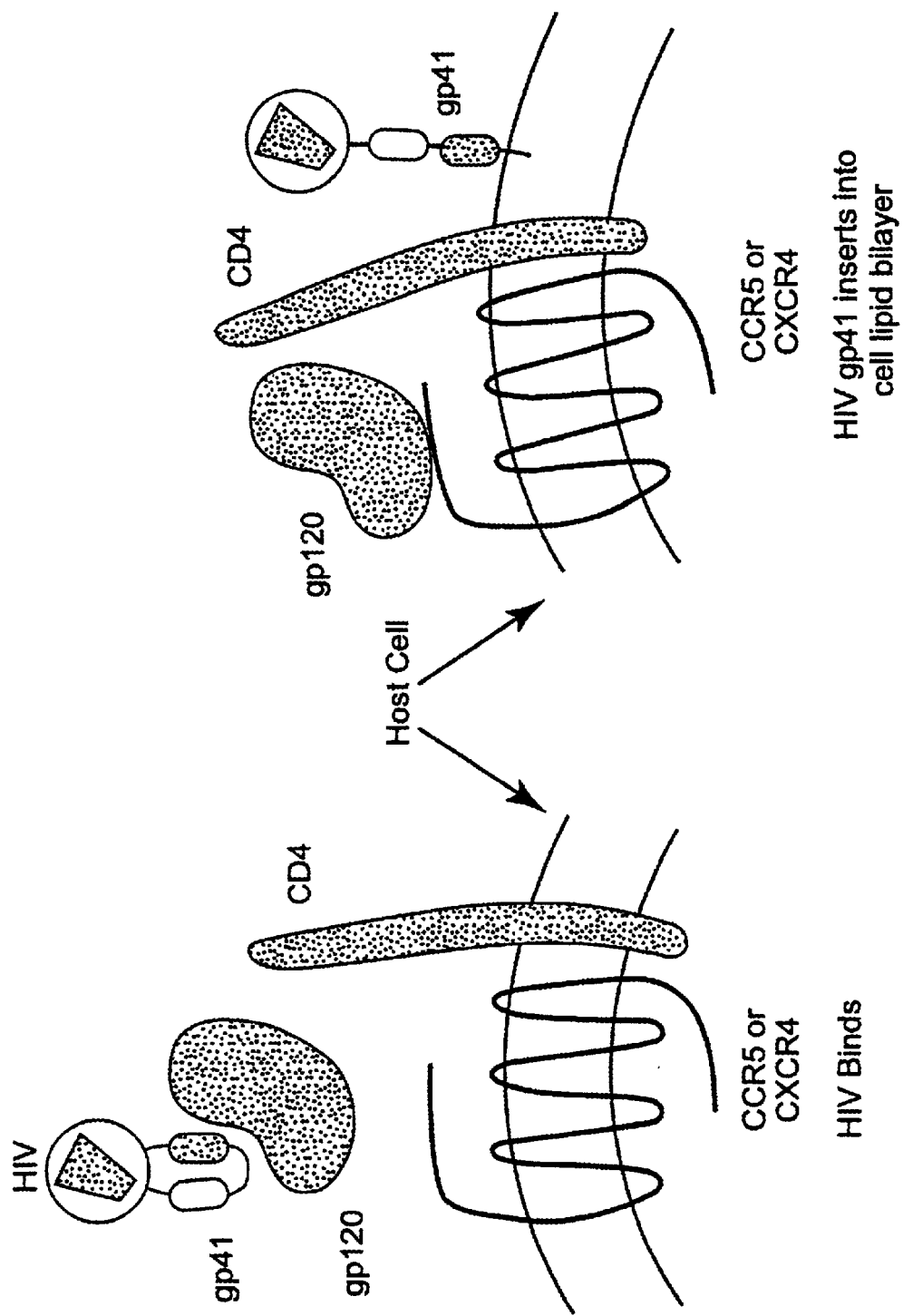

The immunogen of one aspect of the invention comprises HIV envelope cleaved or uncleaved gp140 or gp160 either in soluble form or anchored, for example, in cell vesicles made from gp140 or gp160 expressing cells, or in liposomes containing translipid bilayer HIV gp140 or gp160 envelope. Alternatively, triggered gp160 in aldrithio 1-2 inactivated HIV-1 virions can be used as an immunogen. The gp160 can also exist as a recombinant protein either as gp160 or gp140 (gp140 is gp160 with the transmembrane region and possibly other gp41 regions deleted). Bound to gp160 or gp140 can be recombinant CCR5 or CXCR4 co-receptor proteins (or their extracellular domain peptide or protein fragments) or antibodies or other ligands that bind to the CXCR4 or CCR5 binding site on gp120, and/or soluble CD4, or antibodies or other ligands that mimic the binding actions of CD4 (FIG. 1). Alternatively, vesicles or liposomes containing CD4, CCR5 (or CXCR4) (FIG. 2), or soluble CD4 and peptides reflective of CCR5 or CXCR4 gp120 binding sites (FIG. 3). Alternatively, an optimal CCR5 peptide ligand can be a peptide from the N-terminus of CCR5 wherein specific tyrosines are sulfated (Bormier et al, Proc. Natl. Acad. Sci. USA 97:5762 (2001)). The data in FIG. 13 clearly indicate that the triggered immunogen may not need to be bound to a membrane but may exist and be triggered in solution. Alternatively, soluble CD4 (sCD4) can be replaced by an envelope (gp140 or gp160) triggered by CD4 peptide mimetopes (Vitra et al, Proc. Natl. Acad. Sci. USA 96:1301 (1999)). Other HIV co-receptor molecules that "trigger" the gp160 or gp140 to undergo changes associated with a structure of gp160 that induces cell fusion can also be used. (See also FIG. 8.) The data presented in Example 2 demonstrate that ligation of soluble HIV gp140 primary isolate HIV 89.6 envelope with soluble CD4 (sCD4) induced conformational changes in gp41 (see FIG. 13).

In one embodiment, the invention relates to an immunogen that has the characteristics of a receptor (CD4)-ligated envelope with CCR5 binding region exposed but unlike CD4-ligated proteins that have the CD4 binding site blocked, this immunogen has the CD4 binding site exposed (open). Moreover, this immunogen can be devoid of host CD4, which avoids the production of potentially harmful anti-CD4 antibodies upon administration to a host. (See FIGS. 18–25.)

The immunogen can comprise gp120 envelope ligated with a ligand that binds to a site on gp120 recognized by an A32 monoclonal antibodies (mab) (Wyatt et al, J. Virol. 69:5723 (1995), Boots et al, AIDS Res. Hum. Retro. 13:1549 (1997), Moore et al, J. Virol. 68:8350 (1994), Sullivan et al, J. Virol. 72:4694 (1998), Fouts et al, J. Virol. 71:2779 (1997), Ye et al, J. Virol. 74:11955 (2000)). One A32 mab has been shown to mimic CD4 and when bound to gp120, upregulates (exposes) the CCR5 binding site (Wyatt et al, J. Virol. 69:5723 (1995)). Ligation of gp120 with such a ligand also upregulates the CD4 binding site and does not block CD4 binding to gp120. Advantageously, such ligands also upregulate the HR-2 binding site of gp41 bound to cleaved gp120, uncleaved gp140 and cleaved gp41, thereby further exposing HR-2 binding sites on these proteins—each of which are potential targets for anti-HIV neutralizing antibodies.

In a specific aspect of this embodiment, the immunogen comprises soluble HIV gp120 envelope ligated with either an intact A32 mab, a Fab2 fragment of an A32 mab, or a Fab fragment of an A32 mab, with the result that the CD4 binding site, the CCR5 binding site and the HR-2 binding site on gp120 are exposed/upregulated. The immunogen can comprise gp120 with an A32 mab (or fragment thereof) bound or can comprise gp120 with an A32 mab (or fragment thereof) bound and cross-linked with a cross-linker such as 0.3% formaldehyde or a heterobifunctional cross-linker such as DTSSP (Pierce Chemical Company). The immunogen can also comprise uncleaved gp140 or a mixture of uncleaved gp140, cleaved gp41 and cleaved gp120. An A32 mab (or fragment thereof) bound to gp140 and/or gp120 or to gp120 non-covalently bound to gp41, results in upregulation (exposure) of HR-2 binding sites in gp41, gp120 and uncleaved gp140. Binding of an A32 mab (or fragment thereof) to gp120 or gp140 also results in upregulation of the CD4 binding site and the CCR5 binding site. As with gp120 containing complexes, complexes comprising uncleaved gp140 and an A32 mab (or fragment thereof) can be used as an immunogen uncross-linked or cross-linked with cross-linker such as 0.3% formaldehyde or DTSSP. In one embodiment, the invention relates to an immunogen comprising soluble uncleaved gp140 bound and cross linked to a Fab fragment of an A32 mab, optionally bound and cross-linked to an HR-2 binding protein.

The gp120 or gp140 HIV envelope protein triggered with a ligand that binds to the A32 mab binding site on gp120 can be administered in combination with at least a second immunogen comprising a second envelope, triggered by a ligand that binds to a site distinct from the A32 mab binding site, such as the CCR5 binding site recognized by mab 17b. The 17b mab (Kwong et al, Nature 393:648 (1998) available from the AIDS Reference Repository, NIAID, NIH) augments sCD4 binding to gp120. This second immunogen (which can also be used alone or in combination with triggered immunogens other than that described above) can, for example, comprise soluble HIV gp120 envelope ligated with either the whole 17b mab, a Fab2 fragment of the 17b mab, or a Fab fragment of the 17b mab. It will be appreciated that other CCR5 ligands, including other antibodies (or fragments thereof), that result in the CD4 binding site being exposed can be used in lieu of the 17b mab. This further immunogen can comprise gp120 with the 17b mab, or fragment thereof, (or other CCR5 ligand as indicated above) bound or can comprise gp120 with the 17b mab, or fragment thereof, (or other CCR5 ligand as indicated above) bound and cross-linked with an agent such as 0.3% formaldehyde or a heterobifunctional cross-linker, such as DTSSP (Pierce chemical Company). Alternatively, this further immunogen can comprise uncleaved gp140 present alone or in a mixture of cleaved gp41 and cleaved gp120. Mab 17b,or fragment thereof (or other CCR5 ligand as indicated above) bound to gp140 and/or gp120 in such a mixture results in exposure of the CD4 binding region. The 17b mab, or fragment thereof, (or other CCR5 ligand as indicated above)-gp140 complexes can be present uncross-linked or cross-linked with an agent such as 0.3% formaldehyde or DTSSP.

Soluble HR-2 peptides, such as T649Q26L and DP178 (see below), can be added to the above-described complexes to stabilize epitopes on gp120 and gp41 as well as uncleaved gp140 molecules, and can be administered either cross-linked or uncross-linked with the complex.

A series of monoclonal antibodies (mabs) have been made that neutralize many HIV primary isolates, including, in addition to the 17b mab described above, mab IgG1b12 that binds to the CD4 binding site on gp120 (Roben et al, J. Virol. 68:482 (1994), Mo et al, J. Virol. 71:6869 (1997)), mab 2G12 that binds to a conformational determinant on gp120 (Trkola et al, J. Virol. 70:1100 (1996)), and mab 2F5 that binds to a membrane proximal region of gp41 (Muster et al, J. Virol. 68:4031 (1994)). A mixture of triggered envelope immunogens can be used to optimize induction of antibodies that neutralize a broad spectrum of HIV primary isolates. Such immunogens, when administered to a primate, for example, either systemically or at a mucosal site, induce broadly reactive neutralizing antibodies to primary HIV isolates.

Figure 9:
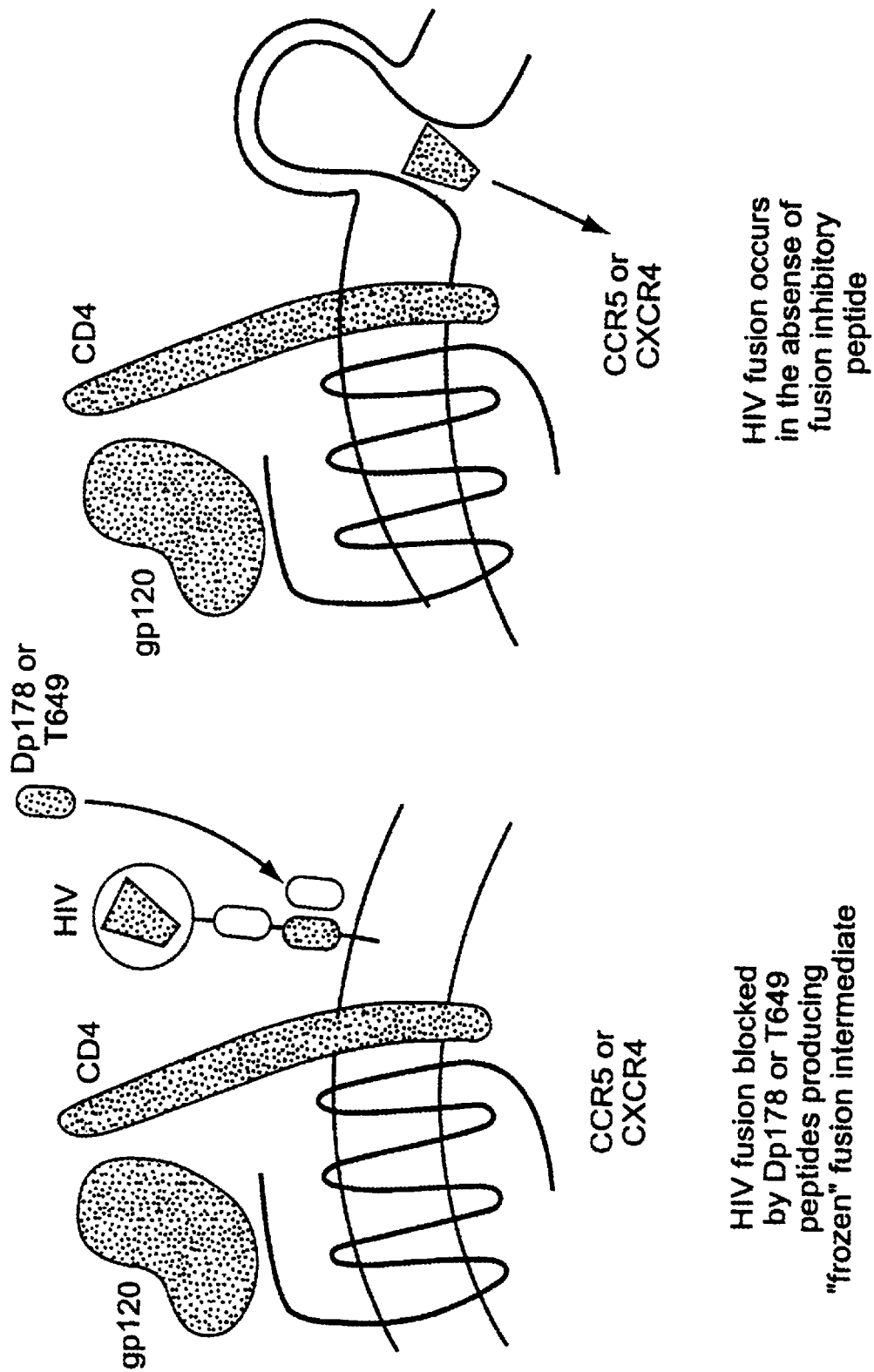

As indicated above, various approaches can be used to "freeze" fusogenic epitopes in accordance with the invention. For example, "freezing" can be effected by addition of the DP-178 or T-649Q26L peptides that represent portions of the coiled coil region, and that when added to CD4-triggered envelop, result in prevention of fusion (Rimsky et al, J. Virol. 72:986–993 (1998) (see FIGS. 9 and 13). HR-2 peptide bound gp140, gp41 or gp160 can be used as an immunogen or crosslinked by a reagent such as DTSSP or DSP (Pierce Co.), formaldehyde or other crosslinking agent that has a similar effect (see below).

"Freezing" can also be effected by the addition of 0.1% to 3% formaldehyde or paraformaldehyde, both protein cross-linking agents, to the complex, to stabilize the CD4, CCR5 or CXCR4, HR-2 peptide gp160 complex, or to stabilize the "triggered" gp41 molecule, or both (LaCasse et al, Science 283:357–362 (1999)).

Further, "freezing" of gp41 or gp120 fusion intermediates can be effected by addition of heterobifunctional agents such as DSP (dithiobis [succimidylproprionate]) (Pierce Co. Rockford, Ill., No. 22585ZZ) or the water soluble DTSSP (Pierce Co.) that use two NHS esters that are reactive with amino groups to cross link and stabilize the CD4, CCR5 or CXCR4, HR-2 peptide gp160 complex, or to stabilize the "triggered" gp41 molecule, or both.

Inherent differences exist in HIV isolates among HIV clades and among HIV isolates from patients in varying geographic locations. Triggered complexes for HIV vaccine development can be made with HIV envelopes from a variety of HIV clades and from a variety of locations. Triggered complexes comprising antibodies or fragments thereof that upregulate the CCR5 binding site, the CD4 binding site, or both, or antibodies, or fragments thereof, that are CD4 inducible can be produced by co-expressing in a dicistronic manner in a plasmid both gp120 and, for example, the heavy and light chain of the Fab region of the antibody, in order to produce a recombinant protein that has the properties of the above described complexes.

The immunogen of the invention can be formulated with a pharmaceutically acceptable carrier and/or adjuvant (such as alum) using techniques well known in the art. Suitable routes of administration of the present immunogen include systemic (e.g. intramuscular or subcutaneous). Alternative routes can be used when an immune response is sought in a mucosal immune system (e.g., intranasal).

Certain aspects of the invention are described in greater detail in the non-limiting Example that follows.

EXAMPLE 1

Figure 4:
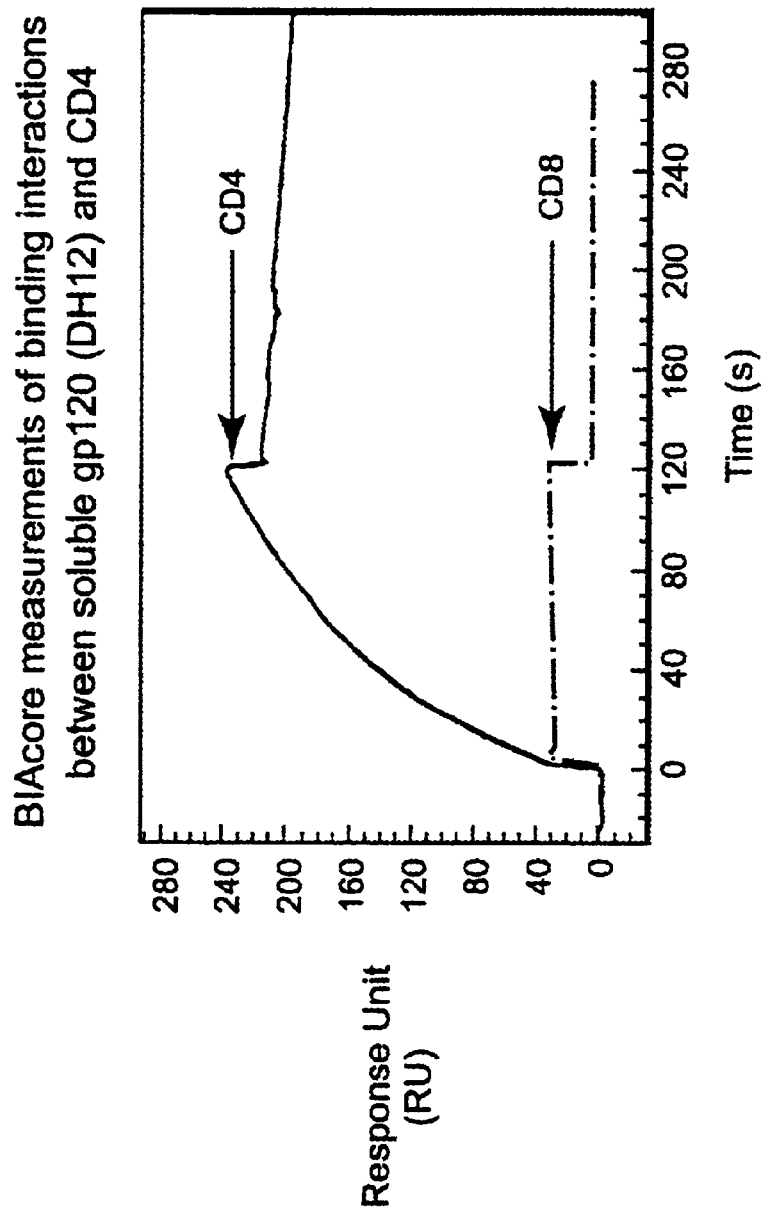
Figure 5:
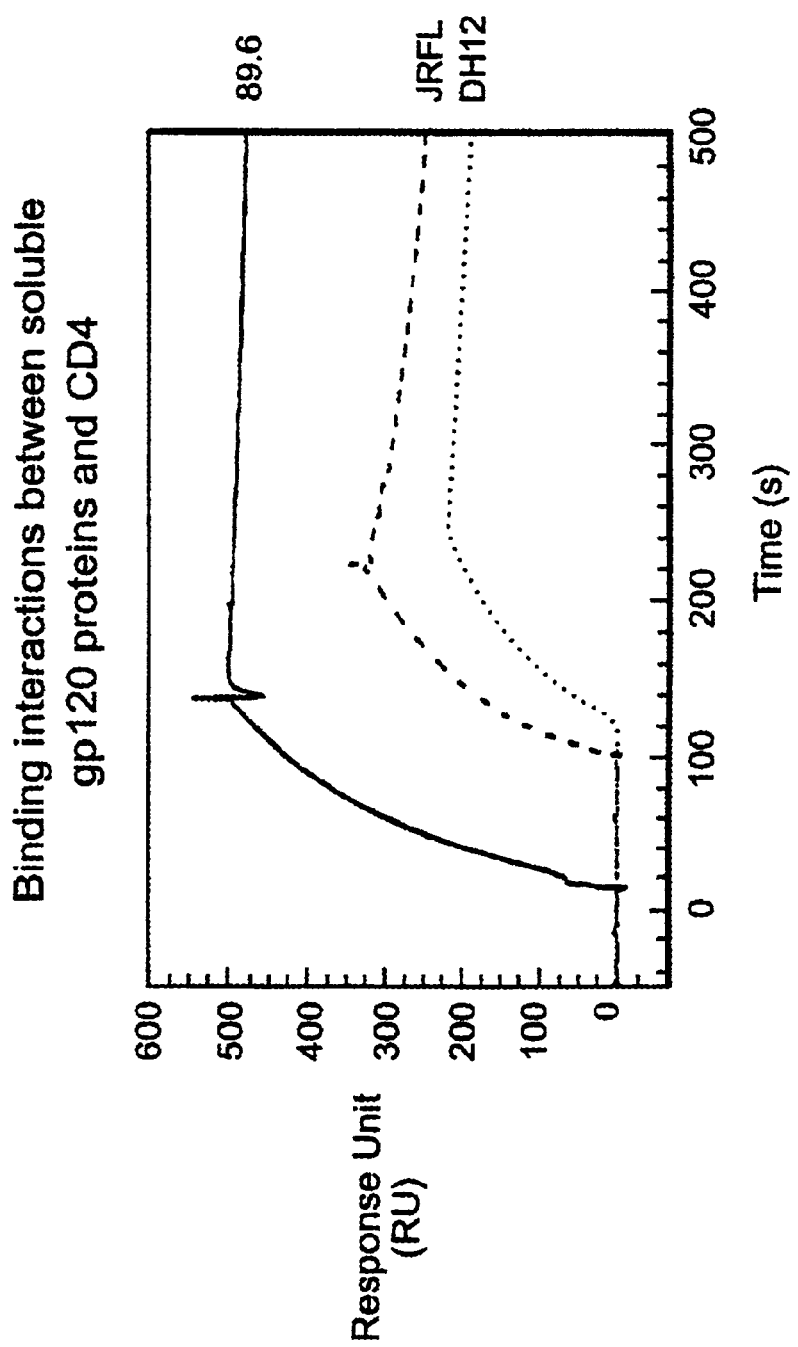
Figure 7:
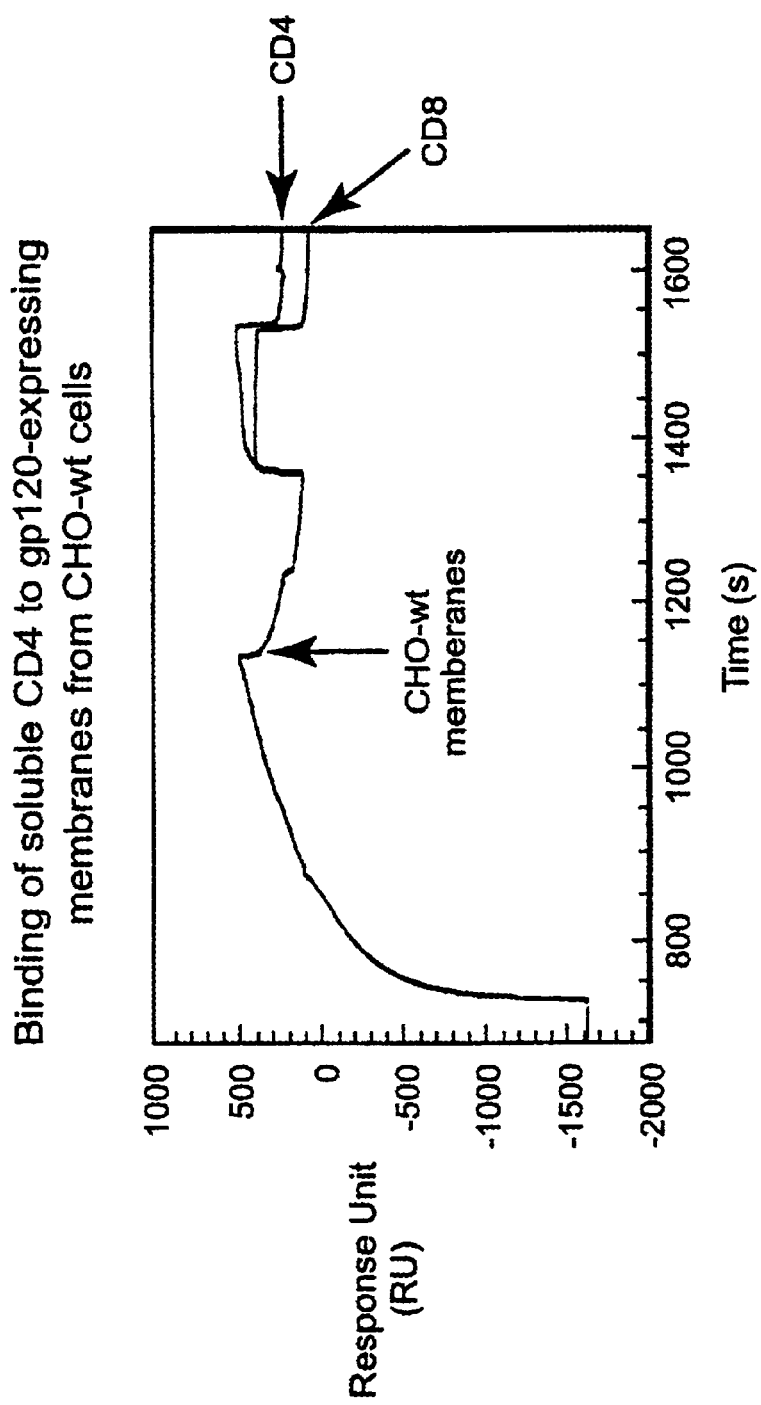

The feasibility of the immunogen production approach of the present invention has been shown using BiaCore 3000 technology. FIG. 4 shows that CD4, not CD8, can be bound to gp120. FIGS. 5, 6 show the differences in interaction of gp120 with the envelop of primary isolates and lab-adapted HIV strains. FIG. 7 shows that vesicles from chimeric hamster ovary cells transfected with HIV-IIIB gp160 and that these vesicles, present on a BiaCore L1 Chip, show stabilized binding of soluble CD4 but not CD8.

EXAMPLE 2

Experimental Details

Proteins

Soluble, monomeric gp120 JRFL, gp120 DH12 and sCD4 were produced by Progenics, and were provided by the Division of AIDS, NIAID, NIH. HIVIIIB gp160 was obtained from Protein Sciences. Envelope proteins from HIV 89.6 (Clade B), and HIV CM235 (Clade E) primary isolates were produced by Pat Earl, NIH, using recombinant vaccinia viruses and purified as described (Earl et al, J. Virol. 68:3015–3026 (1994), Earl et al, J. Virol. 75:645–653 (2001)).

Briefly, BS-C-1 cells in 160 cm² flasks were infected with vBD1(HIV 89.6 gp140) or vBD2 (gp120) vaccinia viruses. After 2 h, the cells were washed in PBS and placed in serum-free OPTI-MEM media (Gibco) for 24–26 hr. The culture medium was then harvested by centrifugation and filtration (0.2 μm) and then TX-100 was added to 0.5% (final conc., v/v). For some of the experiments, the culture medium was concentrated 15–30 fold and served as a source of multimeric gp140 glycoproteins (a mix of cleaved and uncleaved form). Further purification of these glycoproteins was performed using a two-step procedure. In the first step, contaminating proteins were removed and glycoproteins from the medium were bound to a lentil lectin column and eluted with methyl α-D-mannopyranoside. This preparation contained ~50:50 cleaved and uncleaved gp140 and the per-purified culture supernatant concentrate are termed "cleaved gp140". Finally, oligomeric and dimeric gp140 were separated and purified by size exclusion chromatography. This gp140 preparation is termed "uncleaved gp140". The glycoprotein fractions were pooled and concentrated using micro-concentrators.

Monoclonal Antibodies

Human monoclonal antibody against the gp120 V3 loop (19b) the CCR5 binding site (17b), and mab 7B2 against the immunodominant region of gp41 were the gifts of James Robinson (Tulane University, New Orleans, La.). Mabs 2F5, IgG1b12 and 2G12 were obtained from the AIDS References Repository, NIAID, NIH.

CCR5 and HR-2 Peptides

Synthetic peptides were synthesized (SynPep Corporation, Dublin, Calif.), and purified by reverse phase HPLC. Peptides used in this study had greater than 95% purity as determined by HPLC, and confirmed to be correct by mass spectrometry. The CCR5-D1 (MDYQVSSPIYDINYYTSEPCQKINVKQIAAR) (SEQ ID NO:1), peptide was derived from the N-terminus of human CCR5 (Bieniasz et al, EMBO Journal 16:2599–2609 (1997)). Gp41 peptides DP-178 YTSLIHSLIEESQN-QQEKNEQELLELDKWASLWNWF (SEQ ID NO:2) (Wild et al, Proc. Natl. Acad. Sci. USA 91:12676–12680 (1994)), T-649 WMEWDREINNYTSLIHSLIEESQN-QQEKNEQELLEL (SEQ ID NO:3) (Rimsky et al, J. Virol. 72:986–993 (1998)), and T649-Q26L (WMEWDREINNYTSLIHSLIEESQNQLEKNEQELLEL) (SEQ ID NO:4) (Shu et al, Biochemistry 39:1634–1642 (2000)) were derived from HIV-1 envelope gp41 from HIV 89.6 (Collmann et al, J. Virol. 66:7517–7521 (1992)). As a control for HR-2 peptide binding, a scrambled sequence DP178 peptide was made as well.

Surface Plasmon Resonance Biosensor Measurements

SPR biosensor measurements were determined on a BIAcore 3000 (BIAcore Inc., Uppsala, Sweden) instrument. HIV envelope proteins (gp120, gp140, gp160) and sCD4 were diluted to 100–300 mg/ml in 10 mM Na-Acetate buffer, pH 4.5 and directly immobilized to a CM5 sensor chip using standard amine coupling protocol for protein immobilization (Alam et al, Nature 381:616–620 (1996)). Binding of proteins and peptides was monitored in real-time at 25° C. and with a continuous flow of PBS, pH 7.4 at 5–20 ml/min. Analyte (proteins and peptides) were removed and the sensor surfaces were regenerated following each cycle of binding by single or duplicate 5–10 ml pulses of regeneration solution (10 mM glycine-HCl, pH 2.5 or 10 mM NaOH).

All analyses were performed using the non-linear fit method of O'Shannessy et al. (O'Shannessy et al, Anal. Biochem. 205:132–136 (1992)) and the BIAevaluation 3.0 software (BIAcore Inc). Rate and equilibrium constants were derived from curve fitting to the Langmuir equation for a simple bimolecular interaction (A+B=AB).

In preliminary SPR experiments, it was determined that HIV gp120 envelope protein for HIV89.6 bound sCD4 most avidly with relatively little baseline drift ($t_{1/2}$ of binding, 105 min.) compared to HIV gp120 DH12 ($t_{1/2}$ of binding, 25 min) and HIV gp120 JRFL ($t_{1/2}$ of binding 14 min.). Thus, HIV89.6 gp120 and gp140 were produced for subsequent experiments.

Immunoprecipitation of HIV Envelope Proteins Followed by Western Blot Analysis. Soluble HIV 89.6 gp140 or gp120 proteins were incubated with or without 2 μg of recombinant sCD4, and a dose range if either biotinylated DP178 or biotinylated scrambled DP178 as a control in a total volume of 50 μl PBS for 2 h followed by incubation (4 h) with 50 μl suspension of streptavidin-agarose beads (Sigma Chemicals, St. Louis, Mo.). Immune complexes were washed×3 with 500 μl of PBS, resuspended in SDS-PAGE sample buffer containing 2-ME, boiled for 5 min, and loaded onto SDS-PAGE on 4–20% polyacrylamide gels. Gels were transferred to immunoblot membranes for Western blot analysis with either mabs T8 (anti-gp120 N-terminus) or 7B2 (anti-gp41 immunodominant region).

Results

Figure 10A:
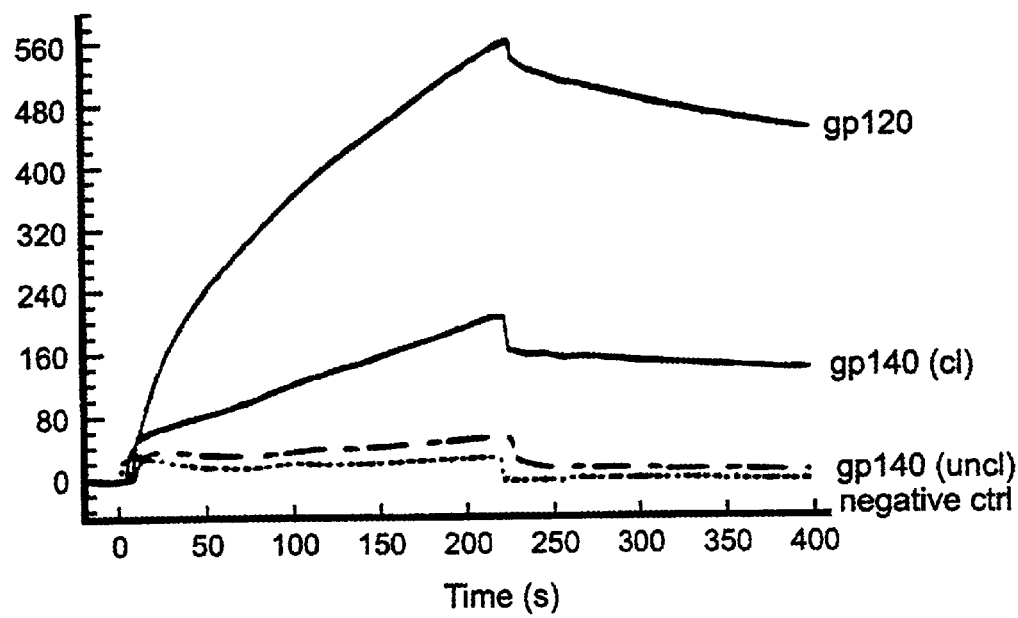
Figure 10B:
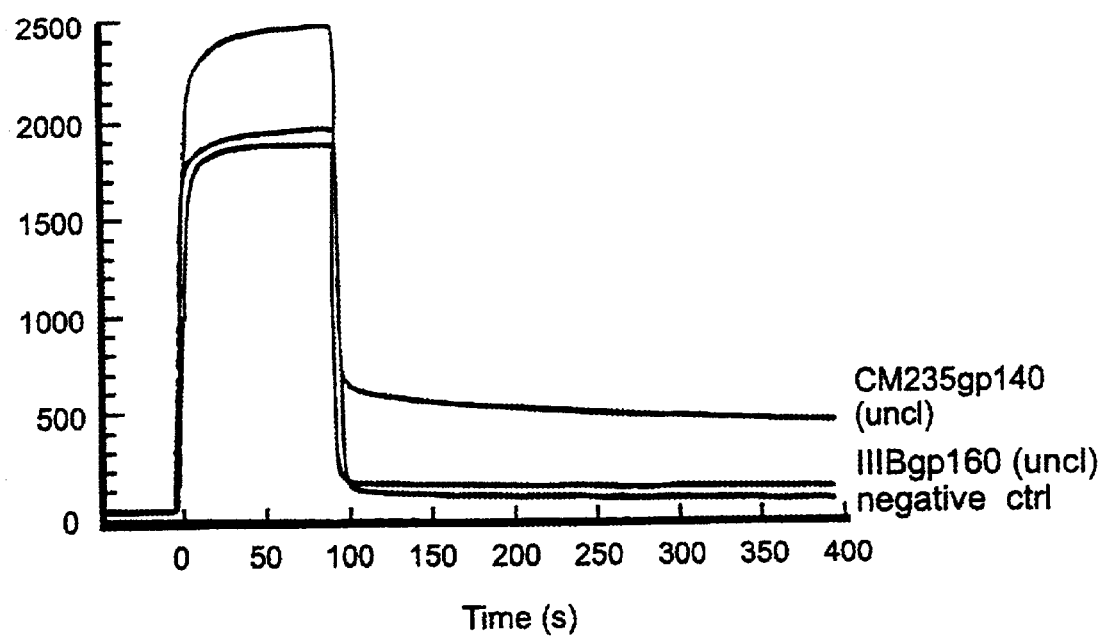

Binding of sCD4 to Cleaved and Uncleaved HIV Envelope. Preliminary SPR studies showed that, of HIV gp120 envelopes JRFL, DH12 and 89.6, the HIV 89.6 gp120 demonstrated the most stable binding to sCD4 (see FIG. 10A). Thus, preparations of HIV89.6 gp140 envelope proteins were studied that contained either cleaved or primarily uncleaved gp140 for binding to sCD4. Non-cleaved HIV CM235 gp140 and, as well, cleaved HIV 89.6 gp140, were tested for their ability to bind sCD4 covalently anchored on the chip in the SPR biosensor assay. Cleaved 89.6 gp140 bound sCD4 well (FIG. 10A). The uncleaved baculovirus-produced HIV IIIB gp160 from Protein Sciences did not bind sCD4 (Mascola et al, J. Infect. Dis. 173:340–348 (1996)) (FIG. 10B). However, cleavage of gp140 into gp120 and truncated gp41 was not an absolute requirement for binding of sCD4 to envelope preparations, as the uncleaved Clade E envelope HIV CM235 gp140 also bound sCD4 (FIG. 10B).

Binding of an N-terminal CCR5 Extracellular Domain Peptide to HIV 89.6 gp140 Envelope. The CCR5 binding site on HIV gp120 is inducible by sCD4 (Kwong et al, Nature 393:648–659 (1998), Rizzuto et al, Science 280:1949–1953 (1998), Wyatt et al, Nature 393:705–710 (1998)). It was next determined if an N-terminal CCR5 extracellular domain synthetic peptide could be made that bound to HIV 89.6 gp140. A 30 aa peptide was produced from the N-terminus of CCR5 (termed CCR5-D1), and tested for ability to bind to cleaved HIV 89.6 gp140.

Figure 10C:
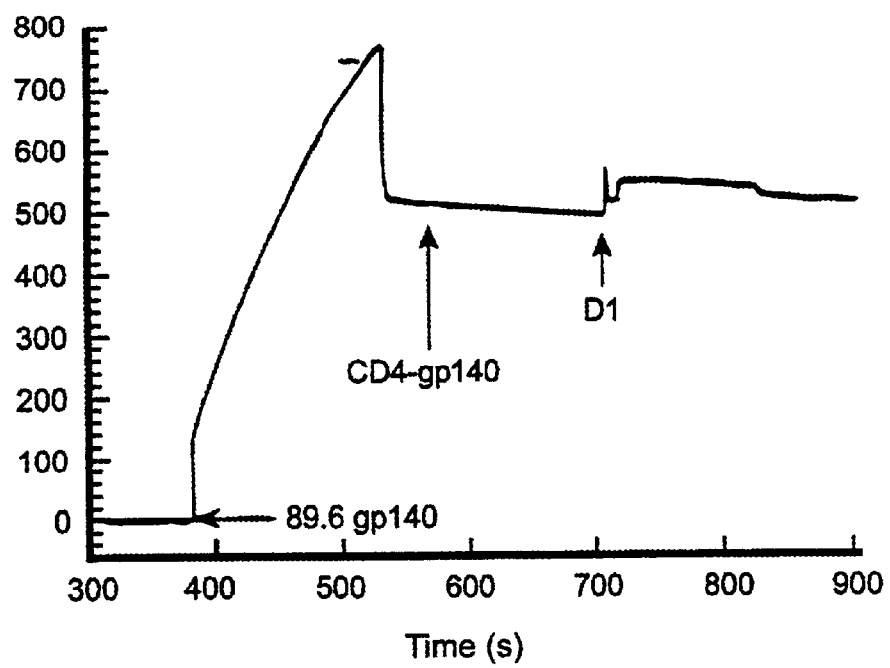
Figure 10D:
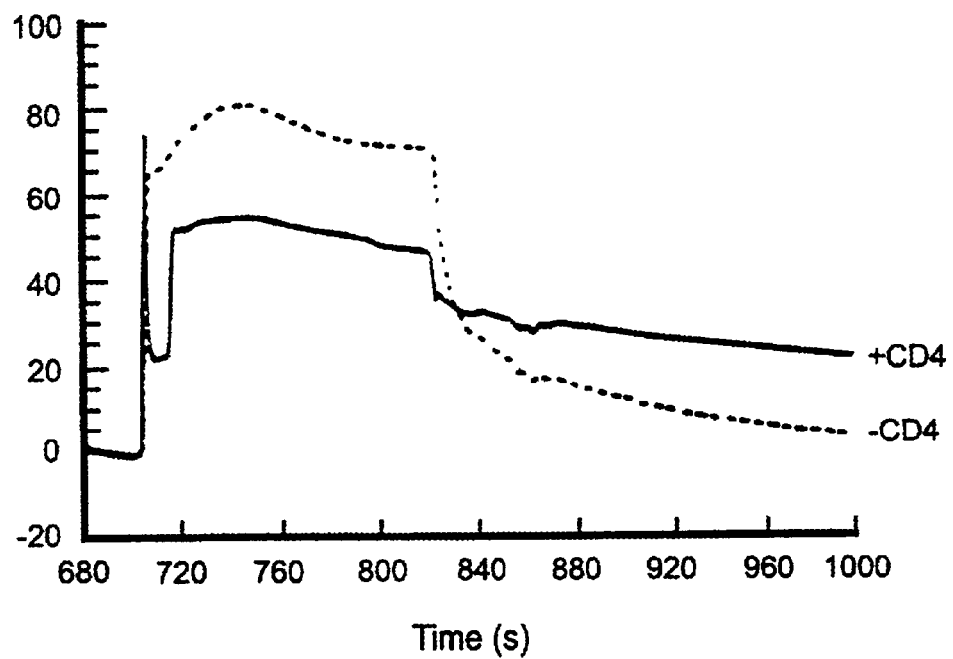

Low levels of constitutive binding of the CCR5-D1 peptide to cleaved gp140 were found, while sCD4 binding to cleaved gp140 envelope induced more stable binding of CCR5-D1 binding to gp140 (FIG. 10C and 10D). Doms et al have found that the affinity of native CCR5 to sCD4 ligated gp120 in the context of membrane bound envelope was 500 µM (Hoffman et al, Proc. Natl. Acad. Sci. 97:11215–11220 (2000)). The binding affinity of this CCR5-D1 N-terminal domain peptide to sCD4-ligated gp140 was found to be ~280 µM (FIG. 10D).

Effect of Soluble CD4 and the CCR5-D1 Extracellular Domain Peptide on the Binding of HR-2 Peptides to Cleaved HIV 89.6 gp140 Envelope Proteins. A major goal of this study was to determine if fusion-associated conformations of gp41 could be detected using SPR assays of HR-2 peptide binding. It was reasoned that if HR-2 peptides can bind gp140, the gp41 coiled-coil structure must be uncoiled, such that endogenous HR-2 is not bound to HR-1. Three such HR-2 peptides were used in this study, DP178 (Wild et al, Proc. Natl. Acad. Sci. USA 91:12676–12680 (1994), Rimsky et al, J. Virol. 72:986–993 (1998)), T-649 (Rimsky et al, J. Virol. 72:986–993 (1998)), and T649Q26L (Shu et al, Biochemistry 39:1634–1642 (2000)). DP178 contains C-terminal amino acids of HR-2 (Wild et al, Proc. Natl. Acad. Sci. USA 91:12676–12680 (1994), Rimsky et al, J. Virol. 72:986–993 (1998)) while T649Q26L contains more N-terminal amino acids of HR-2 (Rimsky et al, J. Virol. 72:986–993 (1998), Shu et al, Biochemistry 39:1634–1642 (2000)). Low level binding DP178 to cleaved HIV 89.6 gp140 was found (FIG. 11A), and DP178 control scrambled peptide did not bind at all (FIG. 11C).

When binding of HR-2 peptides were determined on cleaved gp140 ligated with sCD4, DP178 HR-2 peptide binding was induced on cleaved gp140 by sCD4 (FIG. 11A). Addition of the CCR5-D1 N-terminal peptide to sCD4-gp140 complexes did not significantly change the Kd of DP178 binding to gp140 (0.7 to 1.1 µM) but did slow the on rate of DP178 binding ($7.9 \times 10^{-3}$ M$^{-1}$ s$^{-1}$ to $3.47 \times 10^{-1}$ M$^{-1}$ s$^{-1}$) indicating possibly an induction of protein conformation change (FIGS. 11A, 11B and Table in FIG. 11).

The T649Q26L HR-2 peptide was designed to be of higher affinity for binding to HR-1 by the Q26L substitution (Shu et al, Biochemistry 39:1634–1642 (2000)), and indeed, in this study, T649Q26L also bound to ligated, cleaved CD4-gp140 complexes. Soluble CD4 increased the maximal DP178 binding to cleaved gp140 at equilibrium (Rm) by ~10 fold (from an Rm of DP178 binding with no sCD4 of 35 RU (response units) to an Rm of 320 RU with sCD4) (FIG. 11). The kd, s$^{-1}$ (off-rate) of binding for DP178 to cleaved gp140 after sCD4 was 0.0056. sCD4 binding to cleaved gp140 oligomers resulted in a t½ of DP178 binding of 124 sec. The kd of binding for DP178 to sCD4 and CCR5-D1 ligated cleaved gp140 89.6 was 1.1 µM. An additional control for the specificity of HR-2 peptide binding was the demonstration that the DP178 HR-2 peptide did not bind to sCD4-ligated gp120.

Ability of Biotinylated HR-2 Peptide to Immunoprecipitate HIV Envelope Proteins. To identify the components in gp140 to which HR-2 peptides bind in solution, gp140 envelope was immunoprecipitated with biotinylated DP178 HR-2 peptide, and then the proteins bound to biotinylated HR-2 were analyzed by Western blot analysis. FIG. 12 shows the HIV envelope components present in cleaved HIV 89.6 gp140. Lane 10 shows gp120 and gp140, immunoblotted with anti-gp120 mab T8. Lane 9 shows uncleaved gp140 and gp41 immunoblotted with the anti-gp41 mab, 7B2. FIG. 12 also shows that biotinylated HR-2 peptide, DP178, constitutively immunoprecipitated both cleaved gp41 (~33 kd) and uncleaved gp140 in the absence of sCD4 (lane 3), and the level of gp140 and gp41 immunoprecipitated by biotinylated HR-2 was enhanced by sCD4(lane 1). Lanes 5 and 7 show that the anti-gp120 mab T8 recognized the gp120 region of the gp140 protein immunoprecipitated by biotinylated HR-2. Control immunoprecipitations with scrambled biotinylated DP178 peptide did not immunoprecipitate significant levels of HIV envelope proteins (Lanes 2, 4, 6 and 8). CD-4-Induced Binding of HR-2 Peptides to HIV 89.6 gp140 Envelope Proteins. A major goal of this study was to determine if fusion associated conformations of gp41 could be detected using SPR assays of HR-2 peptide binding. It was reasoned that if HR-2 peptides can bind gp140, the gp41 coiled-coil structure must be uncoiled, such that endogenous HR-2 is not bound to HR-1. Two such HR-2 peptides were used in this study, DP178 (Wild et al, Proc. Natl. Acad. Sci. USA 91:12676–12680 (1994), Rimsky et al, J. Virol. 72:986–993 (1998)) and T649Q26L (Rimsky et al, J. Virol. 72:986–993 (1998), (Shu et al, Biochemistry 39:1634–1642 (2000)). DP178 contains C-terminal amino acids of HR-2 (Wild et al, Proc. Natl. Acad. Sci. USA 91:12676–12680 (1994), Rimsky et al, J. Virol. 72:986–993 (1998)) while T649Q26L contains more N-terminal amino acids of HR-2 (Rimsky et al, J. Virol. 72:986–993 (1998), (Shu et al, Biochemistry 39:1634–1642 (2000)).

HIV envelope gp120 proteins bind to sCD4 with a relatively high affinity (Myszka et al, Proc. Natl. Acad. Sci. USA 97:9026–9031 (2000), Collman et al, J. Virol. 66:7517–7521 (1992)). In preliminary studies, it was found that soluble HIV 89.6 gp120 protein bound strongly to immobilized sCD4, with a $K_d$ 23 nM and with an off-rate of $1.1 \times 10^{-4}$ s$^1$. Thus, a CD4 immobilized surface allowed a very stable capture of HIV envelope, and this approach has been used to assay HR-2 peptide binding to sCD4 bound HIV 89.6 envelope proteins. To create equivalent surfaces of tethered gp140 and gp120 on CM5 sensor chips, sCD4 and anti-gp120 mab T8 immobilized on sensor chips were used as capture surfaces. A blank chip served as an in-line reference surface for subtraction of non-specific binding and bulk responses. Mab T8 bound HIV 89.6 gp120 with an affinity of 5.6 nM. Thus, both CD4 and the mab T8 provided stable surfaces for anchoring HIV envelope proteins.

Since HIV 89.6 gp140 contains both cleaved and uncleaved gp140, it was important to show that gp41 was present in CD4-gp140 complexes following capture of gp140 proteins on CD4 or mab T8 surfaces. When equivalent response unit (RU) amounts of gp140 proteins were captured on these two surfaces (FIG. 14A), the same level of anti-gp120 V3 mab 19b and anti-gp41 mab 2F5 binding was observed (FIGS. 14B and 14C). Mab 2F5 reactivity could either be reacting with captured cleaved gp41 or binding to gp41 in uncleaved gp140. Nonetheless, the captured gp140 proteins on both of these surfaces were near identical in their reactivity with anti-gp120 and anti-gp41 mabs.

The ability of HR-2 peptides to bind to captured gp140 on mab T8 or sCD4 surfaces was tested. Binding of the HR-2 peptides showed qualitative differences in binding to mab T8 and sCD4-bound gp140. Compared to the T8-gp140 surface (near background binding), the DP178 HR-2 peptide bound specifically to the sCD4-gp140 surface (FIG. 14D). However, there was no binding of the scrambled DP178 peptide to mab T8-gp140 or sCD4-gp140 surfaces (FIG. 14D). Similar to HR-2 peptide DP178 binding, HR-2 peptide T649Q26L showed no binding to the mab T8-gp140 surface, and marked binding to the sCD4-gp140 surface (FIG. 14F). Taken together, these results demonstrated that sCD4 induced the binding of both HR-2 peptides, DP178 and T649Q26L, to HIV 89.6 gp140.

HR-2 peptide binding to CD4-gp140 compared to CD4-gp120 complexes. Kowalski et al. have shown that mutations in gp41 HR-2 disrupt gp41-gp120 binding, and that HR-2 contains a touch point site of gp41 non-covalent interaction with gp120 (Alam et al, Nature 381:616–620 (1996)). Thus, it was of interest to compare HR-2 binding to sCD4-gp140 complexes with sCD4-gp120 complexes in SPR assays. As in experiments in FIG. 14, HIV 89.6 gp120 or gp140 proteins were captured in equivalent amounts on sCD4 immobilized surfaces. Interestingly, specific binding of HR-2 peptide was detected on both sCD4-gp140 and sCD4-gp120 surfaces (FIGS. 15A and 15B). However, there was much higher binding of both DP178 and T649Q26L HR-2 peptides to the sCD4-gp140 surface compared to the sCD4-gp120 surface (FIGS. 15A, 15B). To determine if the binding of HR-2 peptides to gp120 was induced by sCD4, HR-2 binding to sCD4-gp120 was compared with HR-2 binding to gp120 proteins captured on the T8 mab surface. As shown in FIG. 15C, the binding of both HR-2 peptides DP178 and T649Q26L to gp120 was specifically induced by sCD4 since neither HR-2 peptide bound to gp120 on the T8 mab surface. No binding of scrambled DP178 to CD4-gp140 or CD4-gp120 was detected (FIG. 15D).

Finally, to assess the affinity of the binding interactions between HR-2 peptide and sCD4 triggered HIV 89.6 gp140 and gp120, the rate constants were measured and the dissociation constant ($K_d$) for the binding of both HR-2 peptides, DP178 and T649Q26L to sCD-gp140 and sCD4-gp120 (FIGS. 15A, 15B, and 15E). There was little difference in the kinetics of HR-2 peptides binding to sCD4-gp140 and sCD4-gp120, indicating that the higher level of binding of the HR-2 peptide to CD4-gp140 was due to induced binding to HR1-gp41 in addition to binding sites on gp120. The binding affinity of the HR-2 peptides for gp120 and gp140 were between 1.2–2.5 µM. The HR-2 binding was stable with relatively slow off-rates ($t_{1/2}$ values in minutes, 7.7 to 10.5 min) on both sCD4-gp120 and sCD4-gp140 complexes.

Binding of HR-2 peptide to recombinant gp41. To directly determine if HR-2 peptides can constitutively bind to purified gp41, recombinant ADA gp41 was immobilized to a sensor surface and the binding of HR-2 peptide, DP178, determined. The HR-2 peptide DP178 bound well to immobilized gp41 (FIG. 16A), while no binding was observed with the scrambled DP178 peptide (FIG. 16C). To compare the binding of DP178 HR-2 peptide to recombinant gp41 versus HIV 89.6 gp140-sCD4 complex, the equilibrium binding contants (Keq) of HR-2 binding to both were measured. While the Keq of DP178 binding to recombinant gp41 was weak at 26.7 µM (FIG. 16E), the Keq of DP178 binding to sCD4-gp140 was 10 fold stronger at 1.7 µM (FIG. 16F).

Complexes of gp120-gp41 formed on a sensor surface can be induced by sCD4 to upregulate HR-2 peptide binding. In the preparation of HIV 89.6 gp140 envelope, there is uncleaved gp140, and cleaved gp140 components of gp120 and gp41. Thus, it is possible that HR-2 peptide could be induced to bind uncleaved gp140 and/or could be induced to bind to cleaved gp120 and gp41. To directly determine if binding of sCD4 to gp120 that is non-covenlently bound to gp41 can upregulate HR-2 peptide binding to the sCD4-gp120-gp41 complex, recombinant ADA gp41 was immobilized on a sensor chip, and HIV 89.6 gp120 or a gp120 sCD4 mixture was flowed over it. It was found that gp120 bound stably to gp41 (FIG. 17). When HR-2 peptide DP178 was flowed over the gp41-gp120-sCD4 complex, binding of HR-2 was upregulated compared to HR-2 binding to gp41 or to the gp41-gp120 complex (FIG. 17). Thus, sCD4 ligation of gp120 non-covalently bound to gp41 can upregulate either gp41 or gp120, or both, to bind to HR-2.

Neutralizing Epitopes on HIV 89.6 gp140 Before and After Ligation with sCD4. The 2F5 (anti-gp41, ELDKWAS (SEQ ID NO:5)) (Muster et al, J. Virol. 67:6642–6647 (1993)), mab neutralizes HIV primary isolates. Prior to ligation of cleaved 89.6 gp140 with sCD4, it was found that the 2F5 gp41 epitope was exposed. Following sCD4 ligation, the 17b CCR5 binding site epitope (2-4) was upregulated and the 2F5 epitope continued to be expressed.

EXAMPLE 3

Experimental Details

Proteins. Soluble CD4 was produced by Progenics, Tarrytown, N.Y. and was provided by the Division of AIDS, NIAID, NIH. Soluble envelope gp120 (VBD-2) and gp140 (VBD-1) proteins from HIV 89.6 primary isolate were produced using recombinant vaccinia viruses and purified as described (Earl et al, J. Virol. 68:3015–3026 (1994), Earl et al, J. Virol. 75:645–653 (2001)). Briefly, BS-C-1 cells in 160 cm$^2$ flasks were infected with vBD1 (HIV 89.6 gp140) or vBD2 (gp120) viruses. After 2 h, the cells were washed in PBS and placed in serum-free OPTI-MEM media (Gibco) for 24–26 hr. The culture medium was then harvested by centrifugation and filtration (0.2 µm) and Tritox-X 100 added to 0.5%. For some experiments, culture medium was concentrated 15–30 fold and served as a source of gp140 glycoproteins (a mix of cleaved and uncleaved forms). Lentil lectin column purified gp140 contained ~50:50 cleaved and uncleaved gp140. Recombinant HIV ADA gp41 protein was obtained from Immunodiagnostics Inc. (Woburn Mass.). HIV-1 gp120 was produced by ABL and provided by the Division of AIDS, NIAID, NIH.

Monoclonal Antibodies. Mab A32 was obtained from James Robinson (Tulane University, New Orleans, La.) (Boots et al, AIDS Res. Hum. Res. 13:1549 (1997)). A32 mab was affinity purified from serum-free media using a Staph Protein-G column.

HR-2 Peptides. Synthetic peptides were synthesized (SynPep, Inc., Dublin, Calif.), and purified by reverse phase HPLC. Peptides used in this study had greater than 95% purity as determined by HPLC, and confirmed to be correct by mass spectrometry. gp41 peptides DP178, YTSLIH-SLIEESQNQQEKNEQELLELDKWASLWNWF (SEQ ID NO:2) (Wild et al, Proc. Nati. Acad. Sci. USA 19:12576–12680 (1994)), and T649-Q26L, WMEW-DREINNYTSLIHSLIEESQNQLEKNEQELLEL (SEQ ID NO:4) (Rimsky et al, J. Virol. 72:986–993 (1998), Shu et al, Biochemistry 39:1634–1642 (2000)) were derived from HIV-1 envelope gp41 from HIV 89.6 (Collman et al, J. Virol. 66:7517–7521 (1992)). As a control for HR-2 peptide binding, a scrambled sequence DP178 peptide was made. For immunoprecipitations and select SPR experiments, biotinylated DP178 and DP178 scrambled peptides were synthesized (SynPep, Inc.).

Surface Plasmon Resonance Biosensor Measurements. SPR biosensor measurements were determined on a BIAcore 3000 (BIAcore Inc., Uppsala, Sweden) instrument. Anti-gp120 mab (T8) or sCD4 (100–300 µg/ml) in 10 mM Na-Acetate buffer, pH 4.5 were directly immobilized to a CM5 sensor chip using a standard amine coupling protocol for protein immobilization (Alam et al, Nature 381:616–620

(1996)). A blank in-line reference surface (activated and de-activated for amine coupling) was used to subtract non-specific or bulk responses. Binding of proteins and peptides (biotinylated or free DP178, T649Q26L, DP178-scrambled) was monitored in real-time at 25° C. with a continuous flow of PBS (150 mM NaCl, 0.005% surfactant p20), pH 7.4 at 10–30 µl/min. Analyte (proteins and peptides) were removed and the sensor surfaces were regenerated following each cycle of binding by single or duplicate 5–10 µl pulses of regeneration solution (10 mM glycine-HCl, pH 2.5 or 10 mM NaOH).

All analyses were performed using the non-linear fit method of O'Shannessy et al. (O'Shannessy et al, Anal. Biochem. 205:132–136 (1992)) and the BIAevaluation 3.0 software (BIAcore Inc). Rate and equilibrium constants were derived from curve fitting to the Langmuir equation for a simple bimolecular interaction (A+B=AB).

Results

CD4-induced binding of HR-2 Peptides to HIV 89.6 gp140 Envelope Proteins. A major goal of this study was to determine if fusion-associated conformations of gp41 could be detected using SPR assays of HR-2 peptide binding. It was reasoned that if HR-2 peptides can bind gp140, the gp41 coiled-coil structure must be uncoiled, such that endogenous HR-2 is not bound to HR-1. Two such HR-2 peptides were used in this study, DP178 (Wild et al, Proc. Natl. Acad. Sci. USA 19:12676–12680 (1994), Rimsky et al, J. Virol. 72:986–993 (1998)) and T649Q26L (Rimsky et al, J. Virol. 72:986–993 (1998), Shu et al, Biochemistry 39:1634–1642 (2000)). DP178 contains C-terminal amino acids of HR-2 (Wild et al, Proc. Natl. Acad. Sci. USA 19:12676–12680 (1994), (Rimsky et al, J. Virol. 72:986–993 (1998)) while T649Q26L contains more N-terminal amino acids of HR-2 (Rimsky et al, J. Virol. 72:986–993 (1998), Shu et al, Biochemistry 39:1634–1642 (2000)).

HIV envelope gp120 proteins bind to sCD4 with a relatively high affinity (Myszka et al, Proc. Natl. Acad. Sci. 97:9026–9031 (2000), Collman et al, J. Virol. 66:7517–7521 (1992)). In preliminary studies, it was found that soluble HIV 89.6 gp120 protein bound strongly to immobilized sCD4, with a $K_d$ 23 nM and with an off-rate of $1.1 \times 10^{-4}$ s$^1$. Thus, a CD4 immobilized surface allowed a very stable capture of HIV envelope, and this approach has been used to assay HR-2 peptide binding to sCD4 bound HIV 89.6 envelope proteins. To create equivalent surfaces of tethered gp140 and gp120 on CM5 sensor chips, sCD4 and anti-gp120 mab T8 immobilized on sensor chips were used as capture surfaces. A blank chip served as an in-line reference surface for subtraction of non-specific binding and bulk responses. Mab T8 bound HIV 89.6 gp120 with an affinity of 5.6 nM. Thus, both CD4 and the mab T8 provided stable surfaces for anchoring HIV envelope proteins.

Since HIV 89.6 gp140 contains both cleaved and uncleaved gp140, it was important to show that gp41 was present in CD4-gp140 complexes following capture of gp140 proteins on CD4 or mab T8 surfaces. When equivalent response unit (RU) amounts of gp140 proteins were captured on these two surfaces, the same level of anti-gp120 V3 mab 19b and anti-gp41 mab 2F5 binding was observed. Mab 2F5 reactivity could either be reacting with captured cleaved gp41 or binding to gp41 in uncleaved gp140. Nonetheless, the captured gp140 proteins on both of these surfaces were near identical in their reactivity with anti-gp120 and anti-gp41 mabs.

The ability of HR-2 peptides to bind to captured gp140 on mab T8 or sCD4 surfaces was next tested. Binding of the HR-2 peptides showed qualitative differences in binding to mab T8 and sCD4-bound gp140. Compared to the T8-gp140 surface (near background binding), the DP178 HR-2 peptide bound specifically to the sCD4-gp140 surface. However, there was no binding of the scrambled DP178 peptide to mab T8-gp140 or sCD4-gp140 surfaces. Similar to HR-2 peptide DP178 binding, HR-2 peptide T649Q26L showed no binding to the mab T8-gp140 surface, and marked binding to the sCD4-gp140 surface. Taken together, these results demonstrated that sCD4 induced the binding of both HR-2 peptides, DP178 and T649Q26L, to HIV 89.6 gp140.

The A32 mab has been reported to reproduce the effect of sCD4 in triggering HIV envelope to upregulated the availability of CCR5 binding site (Wyatt et al, J. Virol 69:5723 (1995)). Thus, an A32 mab surface was used to determine if A32 mab could mimic sCD4 to upregulate HR-2 binding to captured gp140. Similar to sCD4, HR-2 peptide binding was markedly upregulated when gp140 (a mixture of uncleaved gp140, cleaved gp120 and cleaved g41) was captured on the A32 mab surface compared to gp140 captured on the mab T8 surface (FIG. 26). Similar results were obtained using A32 mab and gp120.

All documents cited above are hereby incorporated in their entirety by reference.

One skilled in the art will appreciate from a reading of this disclosure that various changes in form and detail can be made without departing from the true scope of the invention.

What is claimed is:

1. An isolated immunogen comprising an HIV envelope protein bound to a ligand, which ligand upregulates at least one of the CD4 binding site and the CCR5 binding site on said protein, wherein said protein is gp120 noncovalently bound to gp41, and wherein said immunogen further comprises an HR-2 peptide bound to said protein.

2. The immunogen according to claim 1 wherein said ligand is an antibody, or Fab2 or Fab fragment thereof.

3. The immunogen according to claim 1 wherein said ligand binds to a $CCR_5$ binding site on gp120 and upregulates a CD4 binding site on gp120.

4. The immunogen according to claim 3 wherein said ligand is an antibody, or $Fab_2$ or Fab fragment thereof.

5. The immunogen according to claim 3 wherein said ligand is monoclonal antibody (mab) 17b, or $Fab_2$ or Fab fragment thereof, or mimic thereof.

6. The immunogen according to claim 1 wherein said ligand upregulates a CCR5 and a CD4 binding site on gp120.

7. The immunogen according to claim 6 wherein said ligand is an antibody, or $Fab_2$ or Fab fragment thereof.

8. The immunogen according to claim 6 wherein said ligand binds to a site on gp120 to which mab A32 binds.

9. The immunogen according to claim 8 wherein said ligand is mab A32, or $Fab_2$ or Fab fragment thereof, or mimic thereof.

10. The immunogen according to claim 1 wherein said protein is in soluble form.

11. The immunogen according to claim 1 wherein said protein is associated with a cell vesicle or liposome.

12. The immunogen according to claim 1 wherein gp120, gp41 and said ligand are crosslinked.

13. The immunogen according to claim 1 wherein gp120, gp41, said ligand and said HR-2 peptide are crosslinked.

* * * * *

SEQUENCE LISTING

<160> NUMBER OF SEQ ID NOS: 5

<210> SEQ ID NO 1
<211> LENGTH: 31
<212> TYPE: PRT
<213> ORGANISM: Artificial Sequence
<220> FEATURE:
<223> OTHER INFORMATION: Description of Artificial Sequence: Human
    Immunodeficiency Virus

<400> SEQUENCE: 1

Met Asp Tyr Gln Val Ser Ser Pro Ile Tyr Asp Ile Asn Tyr Tyr Thr
 1               5                  10                  15

Ser Glu Pro Cys Gln Lys Ile Asn Val Lys Gln Ile Ala Ala Arg
            20                  25                  30

```
<210> SEQ ID NO 2
<211> LENGTH: 36
<212> TYPE: PRT
<213> ORGANISM: Artificial Sequence
<220> FEATURE:
<223> OTHER INFORMATION: Description of Artificial Sequence: Human
      Immunodeficiency Virus

<400> SEQUENCE: 2

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 3
<211> LENGTH: 36
<212> TYPE: PRT
<213> ORGANISM: Artificial Sequence
<220> FEATURE:
<223> OTHER INFORMATION: Description of Artificial Sequence: Human
      Immunodeficiency Virus

<400> SEQUENCE: 3

Trp Met Glu Trp Asp Arg Glu Ile Asn Asn Tyr Thr Ser Leu Ile His
 1               5                  10                  15

Ser Leu Ile Glu Glu Ser Gln Asn Gln Gln Glu Lys Asn Glu Gln Glu
            20                  25                  30

Leu Leu Glu Leu
        35

<210> SEQ ID NO 4
<211> LENGTH: 36
<212> TYPE: PRT
<213> ORGANISM: Artificial Sequence
<220> FEATURE:
<223> OTHER INFORMATION: Description of Artificial Sequence: Human
      Immunodeficiency Virus

<400> SEQUENCE: 4

Trp Met Glu Trp Asp Arg Glu Ile Asn Asn Tyr Thr Ser Leu Ile His
 1               5                  10                  15

Ser Leu Ile Glu Glu Ser Gln Asn Gln Leu Glu Lys Asn Glu Gln Glu
            20                  25                  30

Leu Leu Glu Leu
        35

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Human
      Immunodeficiency Virus

<400> SEQUENCE: 5

Glu Leu Asp Lys Trp Ala Ser
 1               5
```